United States Patent [19]
Denry

[11] Patent Number: 5,994,246
[45] Date of Patent: Nov. 30, 1999

[54] LOW EXPANSION FELDSPATHIC PORCELAIN

[75] Inventor: Isabelle L. Denry, Hilliard, Ohio

[73] Assignee: Ohio State University, Columbus, Ohio

[21] Appl. No.: 08/960,684

[22] Filed: Oct. 30, 1997

Related U.S. Application Data

[60] Provisional application No. 60/031,066, Nov. 15, 1996, and provisional application No. 60/030,292, Nov. 5, 1996.

[51] Int. Cl.[6] .......................... C03C 10/10; A61C 13/083
[52] U.S. Cl. .................................. 501/32; 501/6; 106/3; 433/218; 433/220; 433/202.1; 433/201.1; 433/212.1
[58] Field of Search .................................. 106/35; 501/6, 501/32; 433/218, 220, 202.1, 201.1, 212.1

[56] References Cited

U.S. PATENT DOCUMENTS

| | | | |
|---|---|---|---|
| 4,550,030 | 10/1985 | Ohi et al. | 427/2 |
| 4,604,366 | 8/1986 | Kacicz et al. | 501/6 |
| 4,798,536 | 1/1989 | Katz | 433/212.1 |
| 5,071,801 | 12/1991 | Bedard et al. | 501/128 |
| 5,192,722 | 3/1993 | Bedard et al. | 501/128 |
| 5,204,077 | 4/1993 | Mori et al. | 423/328.2 |

FOREIGN PATENT DOCUMENTS 2153342  8/1985  United Kingdom .

OTHER PUBLICATIONS

Palmer, David C. et al., Phase Transitions in Leucite: X–ray Diffraction Studies, 16 Phys. Chem. Minerals, 714–719 (1989). No month.

Mazzi, Fiorenzo, et al., The crystal structure of tetragonal leucite, 61 Amer. Mineralogist, 108–115 (1976). No month.

Taylor, D. & Henderson, C.M.B., The Thermal Expansion of the Leucite Group of Minerals, 53 Amer. Mineralogist, 1476–1489 (1968). No month.

Martin, R.F. & Lagache, M., Cell Edges and Infrared Spectra of Synthetic Leucites and Pollucites in the System $KAlSi_2O_6$—$RbAlSi_2O_6$—$CsAlSi_2O_6$, 13 Can. Minerologist, 275–281 (1975). No month.

Martin, R.F. & Lagache, M., L'effet du remplacement du potassium par le rubidium sur les parametres de la maille de la sanidine et la leucite, 93 Bull. Soc. fr. Mineral. Cristallogr., 581–582 (1970). No month.

Prasad, A. & Vaidyanathan, T.K. Crystallization of Cubic Leucite by Composition Additives, Paper presented at 19th annual session, American Association for Dental Research (Mar. 9, 1990).

(Abstract)—Dendry, Isabelle. L. et al., Effect of Rubidium–Leucite on the Flexural Strength and Thermal Expansion of Leucite–Reinforced Porcelain, Dental Research Meeting, (Mar. 1996).

(List continued on next page.)

Primary Examiner—C. Melissa Koslow
Attorney, Agent, or Firm—Ann M. Knab, Esq.

[57] ABSTRACT

A feldspathic porcelain composition is provided which comprises a continuous glassy matrix phase and a discontinuous, substantially uniformly dispersed cubic leucite crystalline phase, said composition possessing a fusion temperature of from about 800° to about 1200° C. Methods of making the feldspathic porcelain composition are also provided, said methods comprising the steps of forming an alkali aluminosilicate powder comprising $SiO_2$, $Al_2O_3$, $K_2O$ and $Na_2O$ and at least one metal salt of rubidium, cesium, calcium, strontium, barium or thallium; heating the powder to effect an exchange of alkali cations with metal cations derived from said metal salt to provide a feldspathic porcelain composition which comprises a continuous glassy matrix phase and a discontinuous crystalline phase comprising cubic leucite.

43 Claims, 25 Drawing Sheets

OTHER PUBLICATIONS

Dendry, Isabelle L. & Rosensteil, Stephen F., Phase Transformations in Feldspathic Dental Porcelains, 48 Bioceramics: Materials and Applications 149–156, (1995). No month.

Faust, George T., Phase Transition in Synthetic and Natural Leucite, 43 Schweiz..Mineral.Petrogr.Mitt., pp. 165–195 (1963). No month.

Hirao, Kazuyuki et al., Thermal Expansion and Structure of Leucite–type compounds, 80 J. Phys. Chem., 1612–1616 (1976). No month.

Kriven, Waltraud M., Possible Alternative Transformation Tougheners to Zirconia: Crystallographic Aspects, 71 J. Amer. Cer. Soc., 1021–30 Dec. 1988.

Gallagher, Sarah A. & McCarthy, G.J., High Temperature Thermal Stability of $CsAlSiO_4$, and $CsAlSi_2O_6$ 17 Mat. Res. Bull., 89–94 (1982). No month.

Rouf, M.A. et al., Crystallization of Glasses in the Primary Plan Field of Leucite in the $K_2O$–$Al_2O_3$—$SiO_2$ System, 77 Trans. J. Brit. Ceram. Soc. 36–39 (1978) No month.

Hermansson L. & Carlsson, R., On the Crystallization of the Glassy Phase in Whitewares, 77 Trans. J. Brit. Ceram. Soc. 32–35 (1978) No month.

Hahn, Christoph & Teuchert, K., Importance of the glass ceramic system $K_2O$–$Al_2O_3$–$SiO_2$ in dental porcelain, 57 Ber. Dt. Keram. Ges. 208–214 (1980). No month.

Mackert, J. Rodway Jr., Effects of Thermally Induced Changes on Porcelain–Metal Compatibility, pp. 53–64. No month.

Prasad et al, "Crystallization of Cubic Leucite By Composition Additives", paper presented at 19th Session of Amer. Assoc. Dent. Res., Mar. 9, 1990.

Hahn et al, "Importance of the Glass Ceramic System $K2O$–$Al2O3$–$SiO2$ in Dental Porcelain", Ber. Dt. Ges. No. 9–10, pp. 208–214, 1980.

2

LOW EXPANSION FELDSPATHIC PORCELAIN

This application claims priority of Provisional Application Ser. No. 60/031,066 filed on Nov. 15, 1996 and Provisional Application Ser. NO. 60/030,292 filed on Nov. 5, 1996.

FIELD OF THE INVENTION

This invention relates to a feldspathic porcelain possessing a low coefficient of thermal expansion, to a method for making the low expansion feldspathic porcelain and to dental restorations comprising the low expansion feldspathic porcelain. More particularly, this invention relates to a low expansion feldspathic porcelain comprising cubic leucite, to a simple and efficient method for obtaining said porcelain and to dental restorations comprising said porcelain.

BACKGROUND OF THE INVENTION

Leucite is a crystalline potassium aluminosilicate which, in stable form, possesses a tetragonal configuration at room temperature. Tetragonal leucite, also known as "low leucite", has been employed as a reinforcing agent in feldspathic dental porcelains. Such dental porcelain materials are described in, for example, U.S. Pat. Nos. 4,604,366 and 4,798,536. Since tetragonal leucite possesses a high coefficient of thermal expansion, the resulting feldspathic porcelains comprising tetragonal leucite dispersed therein as a discontinuous phase have correspondingly high coefficients of thermal expansion. For example, the tetragonal leucite-containing feldspathic porcelain powder sold under the trademark Optec™ by Jeneric/Pentron Inc., Wallingford, Conn. can be used to provide a dental porcelain body possessing a coefficient of thermal expansion of about $18.6 \times 10^{-6}/°$ C. when measured at 50 to 550° C.

When tetragonal leucite is heated to about 625° C., it changes to a cubic polymorph and exhibits a volume change of 1.2%. This transformation is reversible. Upon cooling, the cubic leucite crystals revert to the more stable tetragonal polymorph. In contrast to tetragonal leucite, the stabilized cubic phase of leucite, known as "high leucite", which is otherwise unstable at room temperature, possesses a coefficient of thermal expansion of about $3 \times 10^{-6}/°$ C. when measured at 625 to 900° C.

Rouf et al. "Crystallization of Glasses in the Primary Field of Leucite in the $K_2O—Al_2O_3—SiO_2$ System", Trans. J. Brit. Ceram. Soc., 77:36–39 (1978) describe an isothermal heat treatment method of crystallizing cubic leucite in the high viscosity system of $K_2O—Al_2O_3—SiO_2$ for both powder and bulk samples which employs $TiO_2$, $ZrO_2$ and $P_2O_5$ as catalysts. The Rouf et al. method employs the use of high temperatures and long time periods and relies on the presence of large amounts of $K_2O$ (approximately 18 weight percent) in the starting glass composition to form cubic leucite as the only crystalline phase. Bulk samples of the porcelain produced by the method disclosed in Rouf et al. do not comprise cubic leucite substantially uniformly dispersed therein.

Hermansson et al. "On the Crystallization of the Glassy Phase in Whitewares," Trans. J. Brit. Ceram. Soc. 77:32–35 (1978), similarly disclose a heat treatment method of crystallizing cubic leucite in the high viscosity system of $K_2O—Al_2O_3—SiO_2$. Hermansson et al. disclose that high $K_2O$ content, a long firing time and a low content of CaO (approximately 1 weight percent) are required to stabilize the cubic phase of leucite at room temperature.

Prasad et al. "Crystallization of Cubic Leucite By Composition Additives", 19th Annual Session, American Association For Dental Research, (1990), describe a bulk crystallization method for stabilizing cubic leucite at room temperature by the addition of cesium oxide to a feldspathic composition. The method involves heating a raw material mix including cesium oxide to 1550° C. for eight (8) hours, rapidly cooling the melt to 1025° C. holding the resulting material for 1–4 hours isothermally to effect bulk crystallization of cubic leucite crystals followed by bench cooling the composition in air. The compositions disclosed in Prasad et al. are composed of mixtures of cubic leucite and tetragonal leucite and are highly refractory materials that can only be fused at temperatures in excess of 1200° C.

None of the aforementioned prior art methods disclose an ion exchange step.

It is well-known in the art that it is extremely important that the thermal expansion coefficient of a dental porcelain closely match the thermal expansion coefficient of the metal or porcelain material with which it is in contact. Since the leucite-containing dental porcelains of the prior art generally possess high coefficients of thermal expansion, they cannot be employed in combination with materials possessing significantly lower thermal expansion coefficients. For example, low expansion porcelain veneering materials, such as SlipperyGlass® porcelain sold by Jeneric/Pentron, Incorporated (Wallingford, Conn.), cannot be employed with the high expansion leucite-containing dental porcelains of the prior art, such as Optec™ porcelain sold by Jeneric/Pentron, Incorporated (Wallingford, Conn.).

Accordingly, it is an object of the present invention to provide a low expansion feldspathic porcelain and a method whereby a low expansion feldspathic porcelain can be produced. It is a further object of the present invention to provide a cubic leucite-reinforced feldspathic dental porcelain composition which can be utilized in combination with low expansion materials in the fabrication of dental restorations.

SUMMARY OF THE INVENTION

These and further objects of the invention are obtained by the method of making a feldspathic porcelain composition which comprises the steps of: forming an alkali aluminosilicate powder comprising $SiO_2$, $Al_2O_3$, $K_2O$ and $Na_2O$ and at least one metal salt of rubidium, cesium, calcium, strontium, barium, thallium and mixtures thereof; and heating the powder to effect an exchange of alkali cations with metal cations derived from said metal salt to provide, a feldspathic porcelain composition which comprises a continuous glassy matrix phase and a discontinuous crystalline phase comprising cubic leucite.

The resulting feldspathic porcelain composition possesses a coefficient of thermal expansion generally ranging from about 8 to about $16 \times 10^{-6}/°$ C. when measured at 50° to 550° C. The cubic leucite crystallites present in the discontinuous crystalline phase possess an average diameter which ranges from about 0.25 to about 10 microns. The discontinuous crystalline phase represents from about 5 to about 65 weight percent of the composition and is substantially uniformly dispersed throughout the glassy matrix phase.

The feldspathic porcelain composition of the present invention can be utilized in the fabrication of a wide variety of dental restorations. In one embodiment, the feldspathic porcelain composition is employed as a low expansion core of an all-ceramic dental restoration. In another embodiment, the feldspathic porcelain composition can be fused to a low expansion metal alloy framework or low expansion porcelain core to provide a smooth coating thereon. In another embodiment, the feldspathic porcelain composition can be used to fabricate an inlay, onlay or veneer. The phrase "low expansion" utilized herein shall be understood to refer to coefficients of thermal expansion ranging from about 8 to about $16 \times 10^{-6}/°$ C. when measured at 50° to 550° C.

DETAILED DESCRIPTION OF THE PREFERRED EMBODIMENTS

Figure 1:
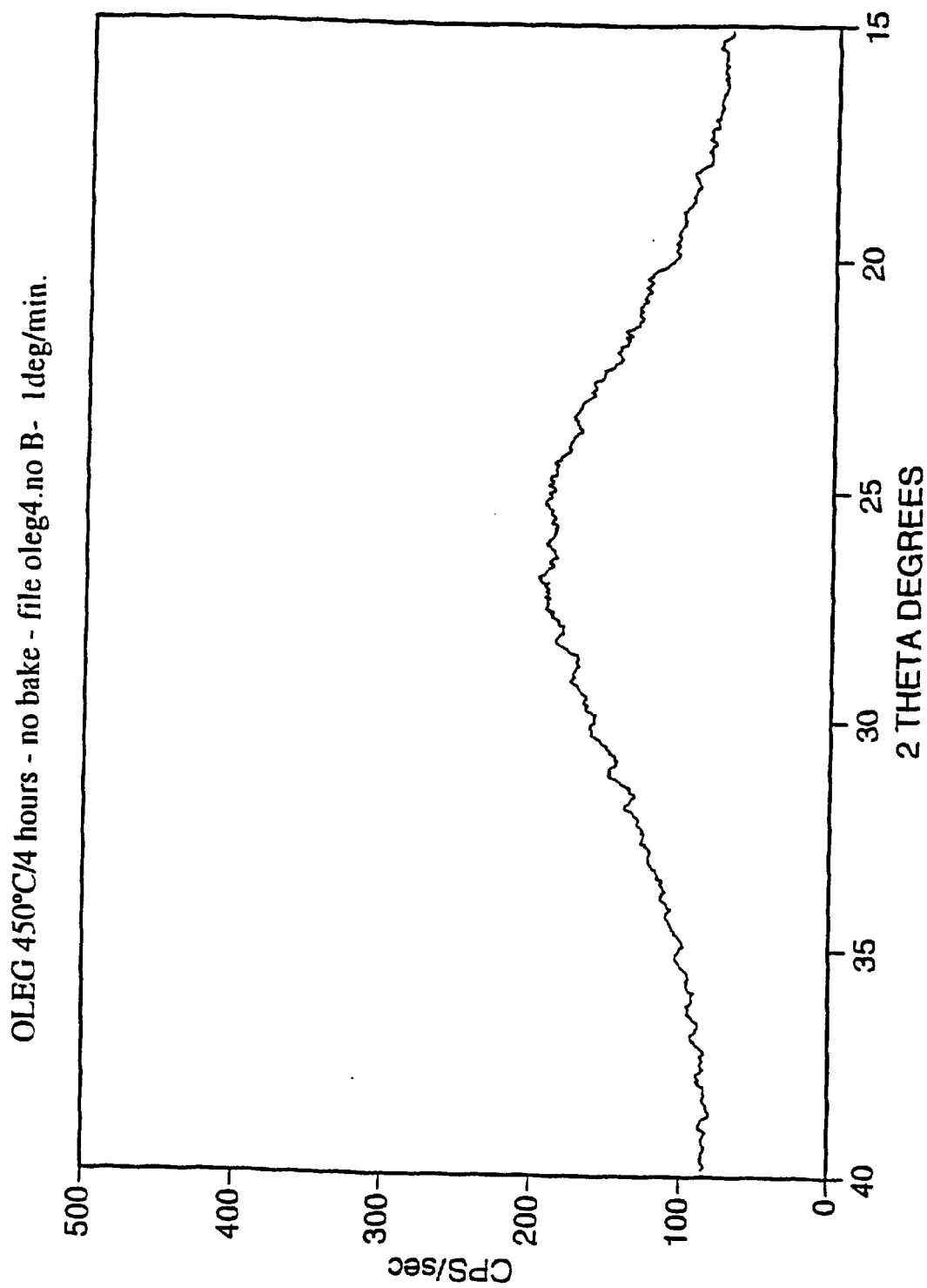
FIGS. 1 and 2 are x-ray diffraction patterns of the amorphous material and feldspathic porcelain composition, respectively, produced in accordance with the method of one embodiment of this invention.

The alkali aluminosilicate powder which is initially formed in accordance with the practice of the present invention comprises an admixture of a feldspathic glass frit comprising $SiO_2$, $Al_2O_3$, $K_2O$ and $Na_2O$ and at least one metal salt of rubidium, cesium, calcium, strontium, barium, or thallium. In one embodiment, the alkali aluminosilicate powder comprises a feldspathic glass frit comprising from about 65 to about 72 weight percent $SiO_2$, from about 9 to about 15 weight percent $Al_2O_3$, from about 5 to about 16 weight percent $K_2O$, from 0.5 to about 10 weight percent $Na_2O$ and from about 20 to about 80 weight percent metal salt (based on the total weight of the alkali aluminosilicate powder) with the remaining components of the powder, if any, including, but not limited to, one or more of $NaNO_3$, $Na_2CO_3$, $Li_2O$, $BaO$, $CaO$, $MgO$, $CeO_2$, $B_2O_3$, $ZrO_2$, $TiO_2$, $ZnO$, $BiO_2$ and $P_2O_5$. Preferably, the alkali aluminosilicate powder is formed by mixing a feldspar glass with a metal salt. The feldspar glass contains, as components thereof, $SiO_2$, $Al_2O_3$, $K_2O$ and $Na_2O$, typically in combination with other components such as, for example, $LiO_2$, $BaO$, $CaO$, $MgO$, $CeO_2$, $B_2O_3$, $ZrO_2$, $TiO_2$, $ZnO$, $BiO_2$ and $P_2O_5$, and the like. Feldspar glasses are well known and can be obtained commercially. In a preferred embodiment, the feldspathic glass frit comprises from about 68.5 to about 71.0 weight percent $SiO_2$, from about 12.0 to about 13.5 weight percent $A_2O_3$, from about 6.5 to about 10.5 weight percent $K_2O$, from about 6.0 to 9.5 weight percent $Na_2O$, from about 0.15 to 2.0 weight percent $CaO$, from 0 to about 0.5 weight percent $MgO$ and from 0 to about 0.4 weight percent $CeO_2$. In a particularly preferred embodiment, the feldspathic glass comprisis 71.0 weight percent $SiO_2$, 12.0 weight percent $Al_2O_3$, 8.0 weight percent $K_2O$, 8.0 weight percent $Na_2O$, 0.2 weight percent $CaO$, 0.4 weight percent $MgO$, and 0.4 weight percent $CeO_2$.

The metal salt utilized in accordance with the practice of this invention can be selected from among the salts corresponding to the general formula:

$$MX$$

wherein M is a metal cation selected from the group consisting of rubidium, cesium, calcium, strontium, barium and thallium and X is an anion selected from the group consisting of nitrate, acetate, sulfate, carbonate and chloride. Rubidium nitrate is particularly preferred in the practice of the method of the present invention. Blends of the metal salt and an alkali metal salt can be advantageously employed in the alkali aluminosilicate powder in accordance with the present invention to facilitate ion exchange. While not wishing to be bound by any theory or mechanism, it is believed that the presence of an alkali metal salt such as sodium nitrate admixed with the metal salt, e.g., rubidium nitrate, i.e., in amounts ranging from about 1 to about 10 weight percent of the metal salt, will promote the ion exchange process by triggering the extraction of sodium from the feldspathic glass frit due to the concentration gradient thereby created. In a highly preferred embodiment of the present invention, rubidium nitrate, sodium nitrate and a feldspar glass comprising:

| Component | Weight Percent |
|---|---|
| $SiO_2$ | about 65 to about 72 |
| $Al_2O_3$ | about 9 to about 15 |
| $K_2O$ | about 5 to about 16 |
| $Na_2O$ | about 0.5 to about 10 |
| $CaO$ | about 0 to about 2 |
| $MgO$ | about 0 to about 2 |
| $CeO_2$ | about 0 to about 0.5 |
| $Li_2O$ | about 0 to about 2 | are utilized to form the alkali aluminosilicate powder in accordance with the practice of the present invention.

Weight ratios of feldspar glass to metal salt of from about 20:80 to about 80:20, respectively, can be utilized to form the alkali aluminosilicate powder in accordance with the practice of the invention. Mixtures of feldspar glass and rubidium nitrate in a weight ratio of about 50:50 have been found to yield particularly good results; however, it is contemplated that the use of other metal salts and/or other weight ratios can be advantageously employed in the method of this invention.

After mixing the feldspar glass and metal salt in a suitable weight ratio, the mixture can be formed into a powder using any suitable technique, e.g., grinding in a mortar. The resulting powder is placed in a furnace where it is heated at a temperature ranging from about 200° to about 900° C., preferably from about 550° to about 650° C. The duration of the heating step can broadly range from about 4 to about 48 hours and may be conducted under vacuum or under pressure, e.g., in an autoclave or a sealed tube, or at atmospheric pressure. The heating step will cause the powder to melt and, as a result, an ion exchange between some or all of the metal cations, e.g., sodium and potassium cations, with some or all of the metal cations derived from the metal salt, e.g., rubidium, will occur. It will be understood by those skilled in the art that the choice of temperature will largely depend on the melting temperature of the metal salt employed. The selection of a suitable temperature is well within the level of skill in the art. While not wishing to be bound by any theory or mechanism, it is postulated that the metal cations diffuse into the glassy matrix and act as nucleating agents for the crystallization and growth of cubic leucite within the glassy matrix.

After the ion-exchange heat treatment operation is performed, the resulting powder can be treated to substantially eliminate unreacted metal salt present therein to provide a purified powder. The phrase "substantially eliminate" utilized herein shall be understood to mean that no metal salt can be detected by x-ray diffraction. Suitable treatment techniques include dissolving and rinsing the powder in a suitable liquid, e.g., distilled water, to eliminate metal salt. The rinsing operation can be repeated until no metal salt can be detected by x-ray diffraction. Thereafter, the resulting purified powder can be dried, for example, at 150° C. for 2 hours.

Ion-exchange is a diffusion driven process and is controlled by the duration as well as the temperature of the heat treatment. The duration of the ion-exchange treatment determines the extent of cubic leucite crystallization in a low expansion feldspar glass.

Thus, for example, in one embodiment of the present invention, the ion-exchange heat treatment can be conducted at relatively low temperatures of from about 200° C. to below about 550° C. for periods of time ranging from about 4 to about 48 hours. Under such conditions, an amphorous (non-crystalline) material is obtained. FIG. 1 is an x-ray diffraction pattern of a specimen of the powder produced in accordance with Example 1 described hereinbelow. FIG. 1 reveals that the material obtained after ion-exchange heat treatment is amorphous (non-crystalline).

The amorphous material is then placed in a furnace and heated, preferably under vacuum, to provide the feldspathic porcelain of this invention. The amorphous material is preferably heated over the temperature range starting at about 550° and rising to about 1200° C. at a heat-up rate ranging from about 0.5° to about 55° C./minute. The vacuum is released when the highest temperature is reached. After the vacuum has been released, the powder may be kept at the highest temperature for about 0 to about 25, preferably about 1 to about 3, minutes after releasing vacuum. In accordance with a preferred embodiment, the amorphous material, prior to being heat treated, is molded into bulk pre-forms using well-known techniques such as mixing the powdered amorphous material in a conventional dental porcelain build-up liquid to form a slurry and manually condensing the slurry in a split mold to form a pre-form possessing desired dimensions. The resulting bulk pre-forms can then be further heated to provide a feldspathic porcelain comprising a discontinuous crystalline phase comprising cubic leucite substantially uniformly dispersed throughout a glassy matrix phase.

Figure 2:
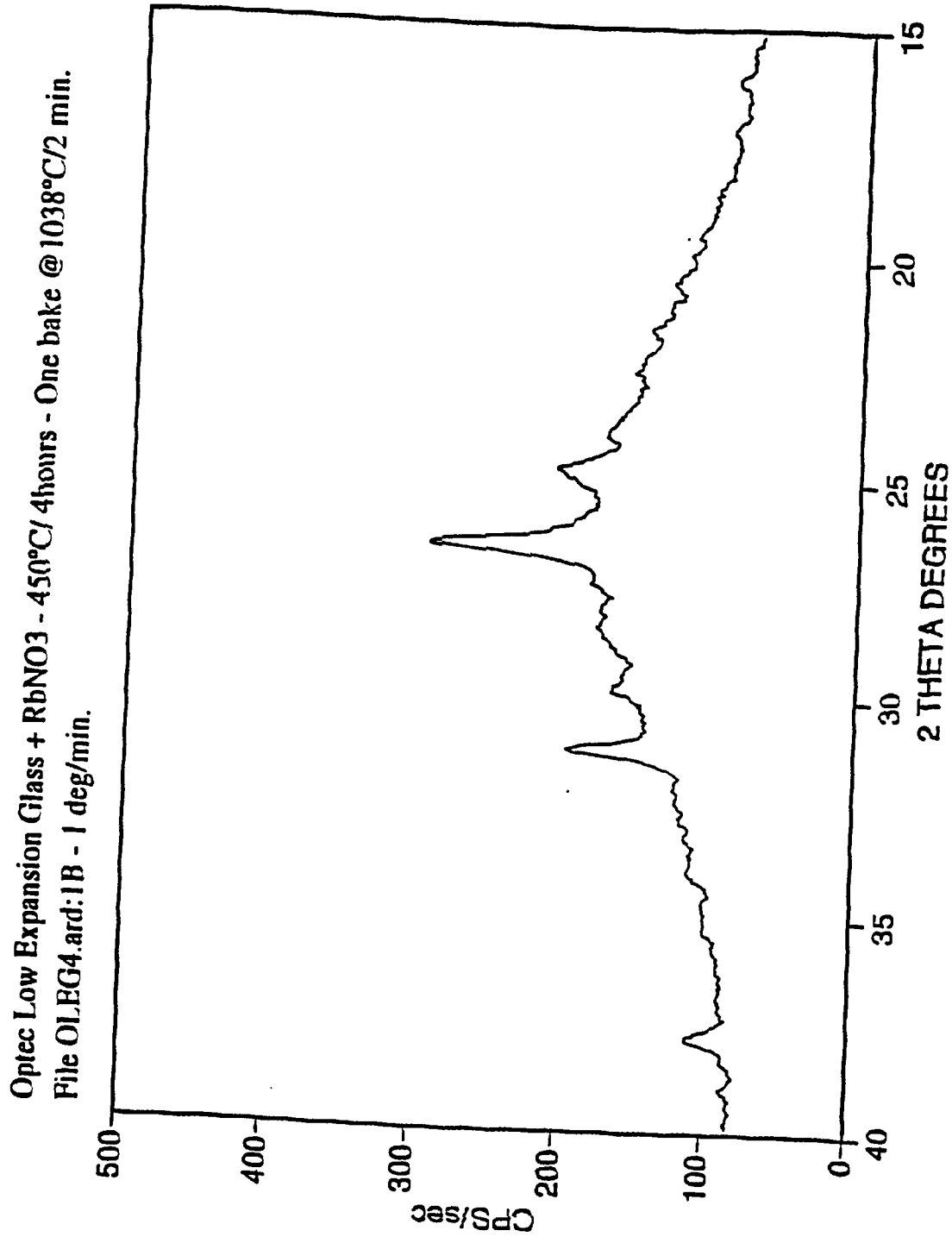
Figure 3:
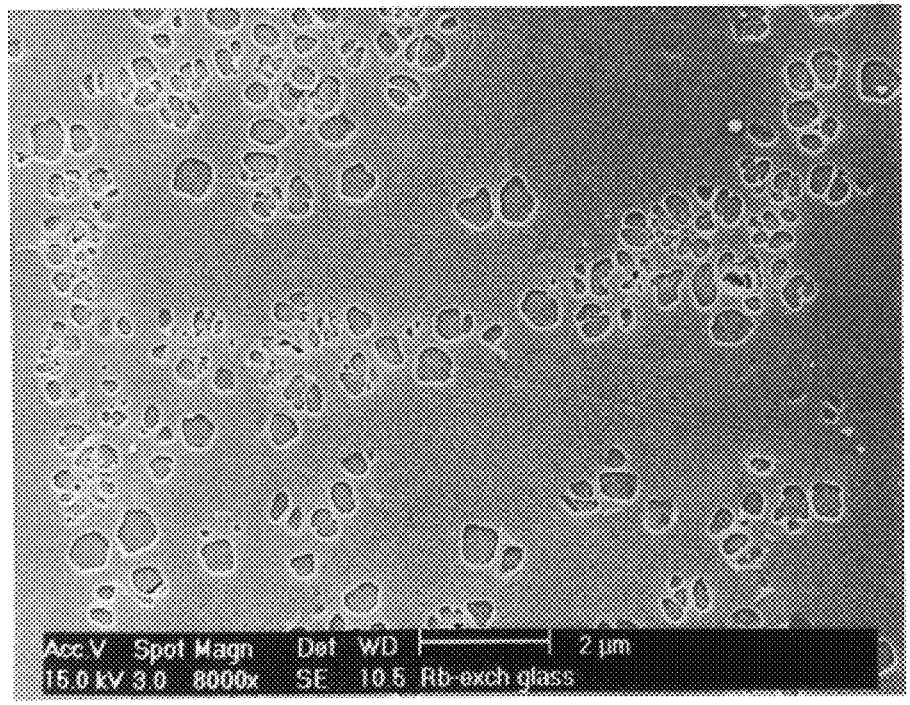
FIG. 3 is an SEM photomicrograph of the feldspathic porcelain composition produced in accordance with the method of one embodiment of this invention.

FIG. 2 is an x-ray powder diffraction pattern of the specimen of Example 1 after such further heating and reveals the presence of cubic leucite in addition to the glassy matrix phase. FIG. 3 is a photomicrograph obtained by scanning electron microscopy (SEM) which confirms the presence of small untwinned cubic leucite crystals possessing an average diameter of between about 0.5 and about 1 micron. An insignificant amount of twinned tetragonal leucite crystals, believed to represent less than 0.05 weight percent of the total composition, may form when practicing the method of the present invention.

In accordance with one feature of the present invention, the amount of the cubic leucite discontinuous crystalline phase can be controlled by adjusting the duration of the ion-exchange heat treatment step. Specifically, it has been discovered that the amount of the crystalline phase increases with the duration of the ion-exchange heat treatment (FIGS. 4($a$)–4($d$)).

One of the significant advantages of the feldspathic porcelain composition herein is that the cubic leucite crystals present therein possess average diameters ranging from about 0.5 to about 10 microns and preferably ranging from about 1 to about 4 microns. Diameters in excess of about 10 microns may impart an undesirably rough and uneven surface and may wear away natural dentition and cause discomfort/irritation inside the oral cavity. The amount of cubic leucite crystals produced ranges from about 5 to about 65, typically from about 20 to about 50, weight percent based on the total weight of the feldspathic porcelain composition. It is contemplated that the amount of cubic leucite crystals may exceed about 65 weight percent of the total composition. The coefficient of thermal expansion of the resulting cubic leucite-containing feldspathic porcelain composition generally ranges from about 8 to about $16 \times 10^{-6}$/° C. when measured at 50° to 550° C. and preferably ranges from about 8 to about $12 \times 10^{-6}$/° C. when measured at 50° to 550° C. In contrast, prior art feldspathic porcelain compositions comprising leucite in the tetragonal form typically possess coefficients of thermal expansion of on the order of about $18.6 \times 10^{-6}$/° C. when measured at 50° to 550° C. The fusion (maturing) temperature of the feldspathic porcelain compositions of the present invention ranges broadly from about 800° to about 1200° C. and typically ranges from about 900° to about 1150° C.

In another embodiment of the present invention, a feldspathic porcelain comprising a discontinuous crystalline phase comprising cubic leucite substantially uniformly dispersed throughout a glassy matrix can be formed directly by heating the powder resulting from the admixture of the alkali aluminosilicate powder and metal salt at a temperature of at least about 550° C. up to about 1200° C. for a time period commensurate with the temperature employed to directly effect cubic leucite formation. Thus, for example, as is seen in the examples, a heat treatment of 550° C. for 48 hours or 650° C. for 8 hours is sufficient to directly give rise to cubic leucite formation.

In accordance with a further embodiment of the method herein, the feldspathic porcelain composition can be further heat treated at a temperature within the range of about 600° to about 1100° C. for about 1 to about 48 hours, preferably from about 1 to about 4 hours. It has been observed that this further heat treatment operation can result in an increase in the amount of the cubic leucite crystalline phase and/or the average particle size of the cubic leucite crystals.

The properties of the feldspathic porcelain composition can be adjusted by applying well-known principles. For example, the coefficient of thermal expansion can be adjusted, if desired, by adjusting the proportion of $SiO_2$ and/or adjusting the proportion of the alkali metal oxides. The fusion point can be adjusted by adjusting the proportion of CaO and/or the alkali metal oxides. For example, an increase in the $Na_2O:K_2O$ ratio lowers the fusion point. It is well within the skill of the ceramics art to apply these principles to make fine adjustments to the thermal expansion coefficient and fusion temperature of the feldspathic porcelain composition herein.

The low expansion feldspathic porcelain composition can be utilized in the fabrication of a wide variety of dental restorations such as all-ceramic restorations, porcelain-fused-to-metal restorations, inlays, onlays and veneers. It is contemplated that the feldspathic porcelain composition can be utilized as a low expansion ceramic core for an all-ceramic restoration. In a particularly preferred embodiment, the powdered feldspathic porcelain composition can be compacted and then sintered at a temperature of from about 600° to about 850° C. to form solid pre-forms (greenwares) or, if desired, fully fused at a temperature of from about 900° to about 1150° C. to form solid pre-forms (whitewares) which can be subsequently injection molded to form dental restorations utilizing the hot pressing technique. This technique is initiated by creating the restoration in wax. The wax pattern is lifted from the die and invested or surrounded by a mix of "plaster-like" material which is allowed to harden. A channel or opening leads from the outer surface of the investment into the wax pattern. Wax is eliminated from the investment during a burnout procedure. The pre-form of the feldspathic dental porcelain (greenware or whiteware) is placed in a special hot press (for example, the Optimal™ Autopress™ hot press available from Jeneric/Pentron, Inc., Wallingford, Conn.) and is softened and forced under pressure into the opening of the investment. The softened material fills the void created by the wax pattern. After cooling, the hardened ceramic is broken out of the investment. Where desired, one or more layers of the porcelain herein can be applied over the ceramic core and/or color can be baked onto the surface of the restoration to simulate tooth color.

Since the porcelain of the present invention possesses a coefficient of thermal expansion of generally below about $16 \times 10^{-6}/°$ C., and typically below about $12 \times 10^{-6}/°$ C., when measured at 50 to 550° C., it can be applied over metal alloy frameworks possessing similarly low coefficients of thermal expansion, for example, titanium metal alloys, or over a low expansion ceramic, for example, aluminous porcelain (available under the trademark Vitadur-N™ Vident, Baldwin Park, Calif.). One or more layers of the porcelain composition can be applied over a low expansion metal alloy framework or ceramic and be separately fired. If desired, an opaque layer of the feldspathic porcelain composition containing an opacifing agent such as $TiO_2$, $SnO_2$, $Al_2O_3$, ZnO, $CeO_2$, and the like can be applied over the framework and fired. Thereafter, or in lieu thereof, or in combination therewith, a shaded layer of the feldspathic porcelain composition containing one or more conventional pigments such as vanadates, manganates, chromates, or other transition metal compounds, can be applied to tint the shaded layer to the desired shade. If desired, a fluorescing agent such as cerium oxide, terbium oxide, yttrium oxide, and the like, or other conventional additives can also be incorporated into the porcelain to simulate natural dentition. The opaque and/or fluorescent shaded layer(s) can then be overcoated (before or after firing), if desired, with the feldspathic porcelain composition of the present invention. In this manner, special effects can be obtained, e.g., a different shade at the tip of the restoration than at the gingival area. The porcelain layers can be applied to the framework in the usual manner, as by applying a paste of the feldspathic porcelain powder in water over the framework, shaping to the desired configuration, and then firing.

The porcelain can also be employed in the form of a dental post, or as an inlay, onlay or veneer to replace amalgam, gold or other porcelains. The feldspathic porcelain of the present invention can be prepared as an inlay, onlay or veneer by building the porcelain powder in the form of an aqueous slurry on an appropriate refractory investment die (such as Synvest™ refractory die sold by Jeneric/Pentron Inc. of Wallingford, Conn.) and then firing the porcelain to a temperature ranging from about 800° to about 1200° C. to effect proper maturation/fusion of the porcelain. If desired, those skilled in the art can use a foil technique wherein a thin (0.001") piece of platinum or other suitable foil adapted to a gypsum die is utilized to hold the porcelain in its proper geometry, the foil/porcelain is removed from the gypsum die and the porcelain is fired to effect proper maturation/fusion of the porcelain. The resultant fused specimen is placed on the prepared tooth and results in a smooth surface in contact with adjacent teeth.

The following examples illustrate the practice of the present invention.

EXAMPLE 1

A low expansion feldspar glass (obtained from American Thermocraft Corp., Somerset, N.J.) comprising:

| Component | Weight % |
| --- | --- |
| $SiO_2$ | 71.0 |
| $Al_2O_3$ | 12.0 |
| $Na_2O$ | 8.0 |
| $K_2O$ | 8.0 |
| CaO | 0.2 |
| MgO | 0.4 |
| $CeO_2$ | 0.4 | was mixed in equal proportions with rubidium nitrate (99%, Johnson Matthey, Ward Hill, Mass.). The powders were ground and mixed in a mortar, placed in a porcelain crucible and heat treated at 450° C. for 4 hours to effect an exchange of sodium and potassium ions derived from the feldspar glass with rubidium ions derived from rubidium nitrate. The resulting ion-exchanged powdered material was then rinsed with water and dried at 150° C. for 2 hours. X-ray diffraction was performed (FIG. 1) after drying and revealed that the material obtained was amorphous.

The amorphous material was mixed into a slurry using dental porcelain build-up liquid (Universal Porcelain™ build-up liquid, Jeneric/Pentron, Inc., Wallingford, Conn.). The slurry was manually condensed into a split mold to form a bar (4×8×25 mm). The bar was heated at a heat-up rate of 55° C. per minute under vacuum in a porcelain oven starting at 600° C. and rising to 1038° C., at which temperature the vacuum was released. The bar was held at 1038° C. at atmospheric pressure for 2 minutes. X-ray powder diffraction was performed on the specimen and revealed the presence of cubic leucite in addition to the glassy phase (FIG. 2). Examination of the specimen by scanning electron microscopy confirmed the presence of small untwinned crystals with a size ranging between about 0.5 and about 1 micrometer (FIG. 3).

EXAMPLES 2–5 AND COMPARATIVE EXAMPLES 1–2

Figure 5:
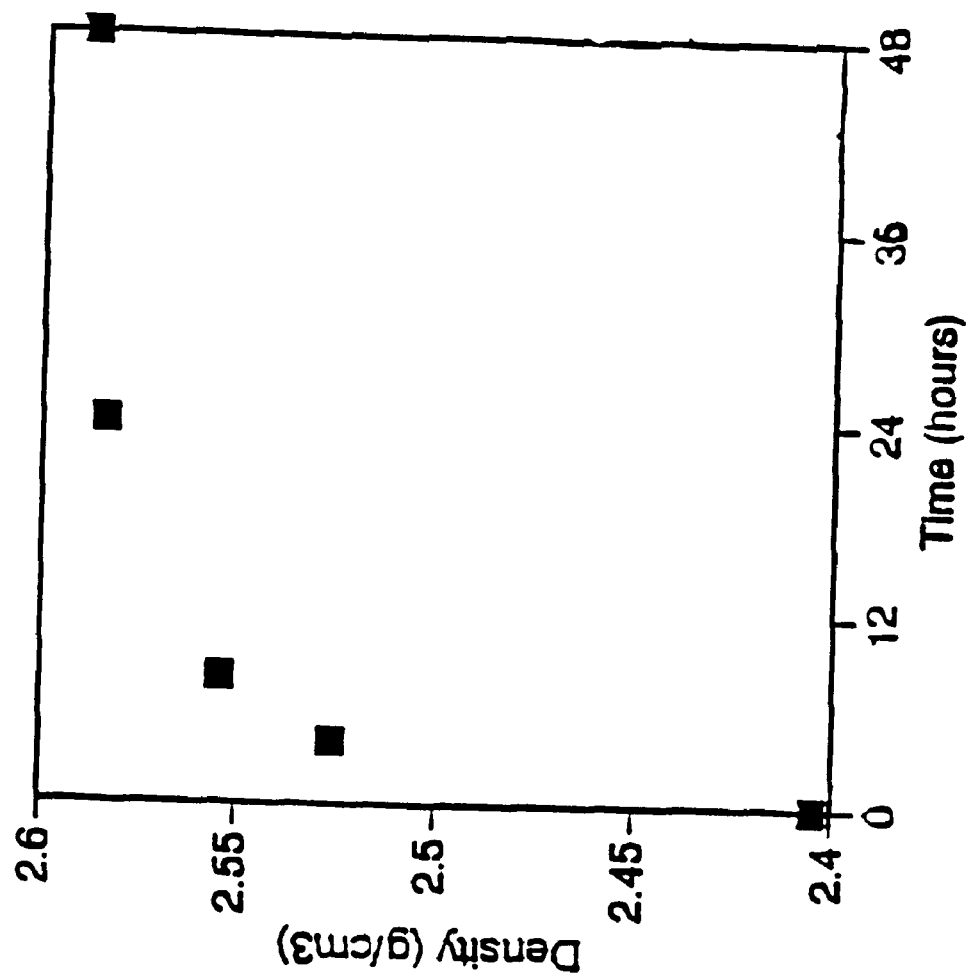
FIG. 5 is a graph which plots mean density of the feldspathic dental porcelain of this invention versus duration of ion-exchange heat treatment in accordance with this invention.

The effect of the duration of the ion-exchange treatment on the percent crystallinity was investigated. The low-expansion feldspar glass was mixed in equal proportions with $RbNO_3$ and heat treated at 450° C. for 4, 8, 24 and 48 hours (Examples 2–5, respectively). X-ray diffraction of the powder exchanged for 48 hours before baking at 1038° C. showed only a glassy phase, thus confirming the amorphous nature of the ion-exchanged materials. The powders were rinsed and dried as described in Example 1. Bars were prepared and heated up to 1038° C. and baked at 1038° C. at atmospheric pressure for 2 minutes as described in Example 1. X-ray powder diffraction of the specimens revealed that the amount of crystalline phase increased with the duration of the heat treatment (FIGS. 4(a) through (d)). Density measurements using Archimedes' method were performed on the bars. The density results, which confirm that the crystalline phase increases as the duration of ion-exchange treatment increases, are listed in Table 1 below. A graph showing the mean density with regard to the duration of the heat treatment is shown in FIG. 5.

TABLE 1

| Example | Average Density |
| --- | --- |
| 2 | 2.526 ± 0.005 |
| 3 | 2.554 ± 0.004 |
| 4 | 2.584 ± 0.006 |
| 5 | 2.588 ± 0.008 |
| Comparative Example 1 | 2.405 ± 0.003 |
| Comparative Example 2 | 2.432 ± 0.006 |

Comparative Example 1 corresponds to bars obtained by manually condensing the feldspar glass of Example 1 into bars (4×8×25 mm) and heating the bars under vacuum in a porcelain oven starting at 600° C. and rising to 1038° C. at a heat-up rate of 55° C. per minute. Vacuum was released at 1038° C. and the bars were baked at 1038° C. at atmospheric pressure for 2 minutes. Comparative Example 2 corresponds to bars obtained by manually condensing Optec™ high strength porcelain (Jeneric/Pentron, Inc., Wallingford, Conn.) into bars (4×8×25 mm) and heating the bars under vacuum in a porcelain oven starting at 600° C. and rising to 1038° C. at a heat-up rate of 55° C. per minute. Vacuum was released at 1038° C. and the bars were baked at 1038° C. at atmospheric pressure for 2 minutes. The density results showed that the ion exchange treatment significantly increased the density of the feldspar glasses (Examples 2–5) compared to the untreated controls (Comparative Examples 1-2), thus indicating that an exchange of sodium and potassium ions with a metal ion such as rubidium has taken place.

Figure 6:
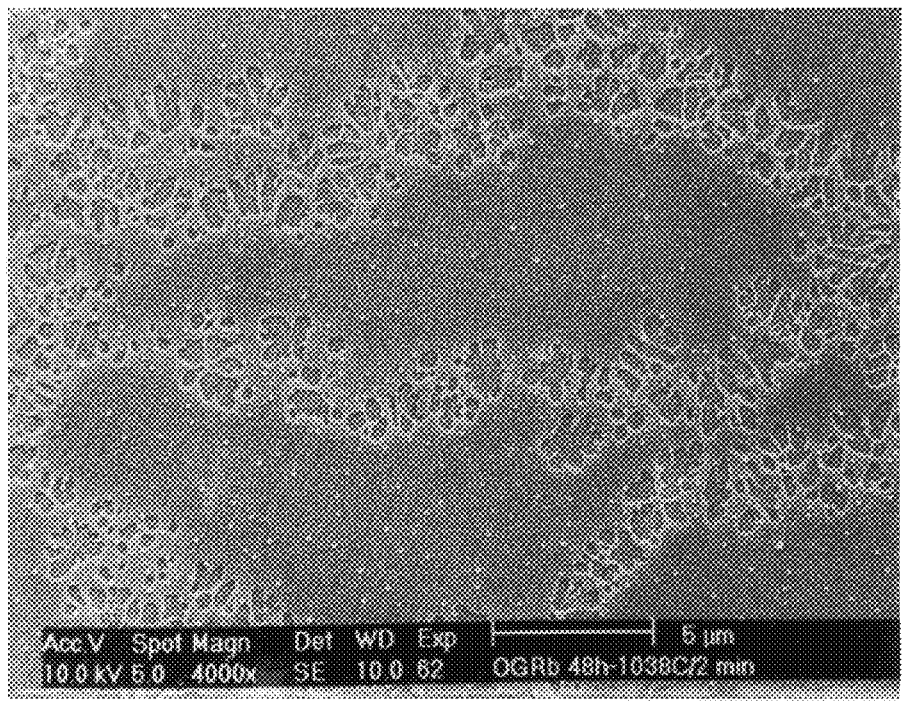
FIG. 6 is a photomicrograph which depicts the microstructure of a specimen obtained by ion-exchange heat treatment for 48 hours followed by heat treatment starting at 600° C. up to 1038° C. for 2 minutes at a heat-up rate of 55° C./minute.
Figure 4A:
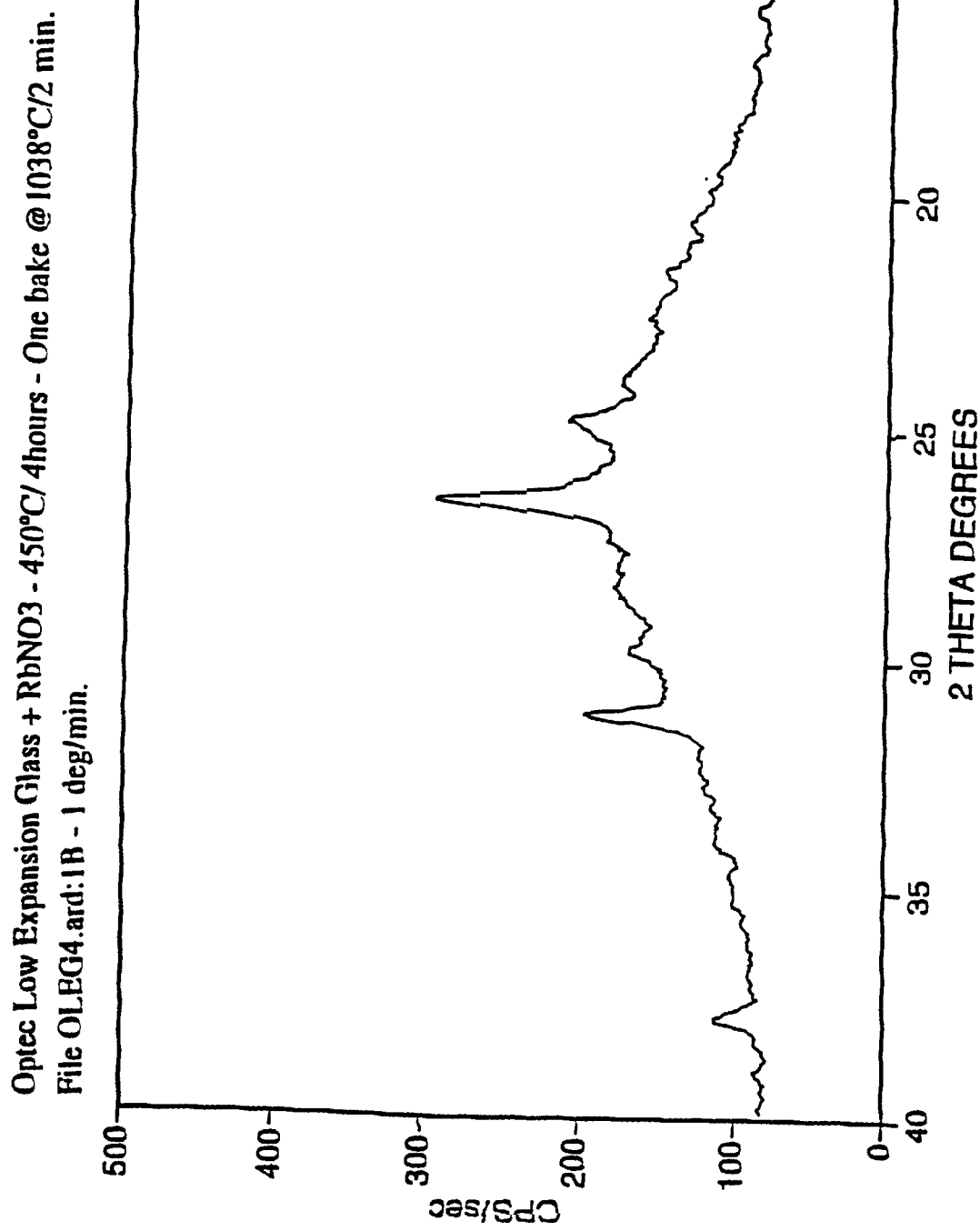
FIGS. 4(a) through 4(d) are x-ray powder diffraction patterns which demonstrate that the amount of discontinuous crystalline phase increases with the duration of the ion-exchange heat treatment in accordance with the present invention.
Figure 4B:
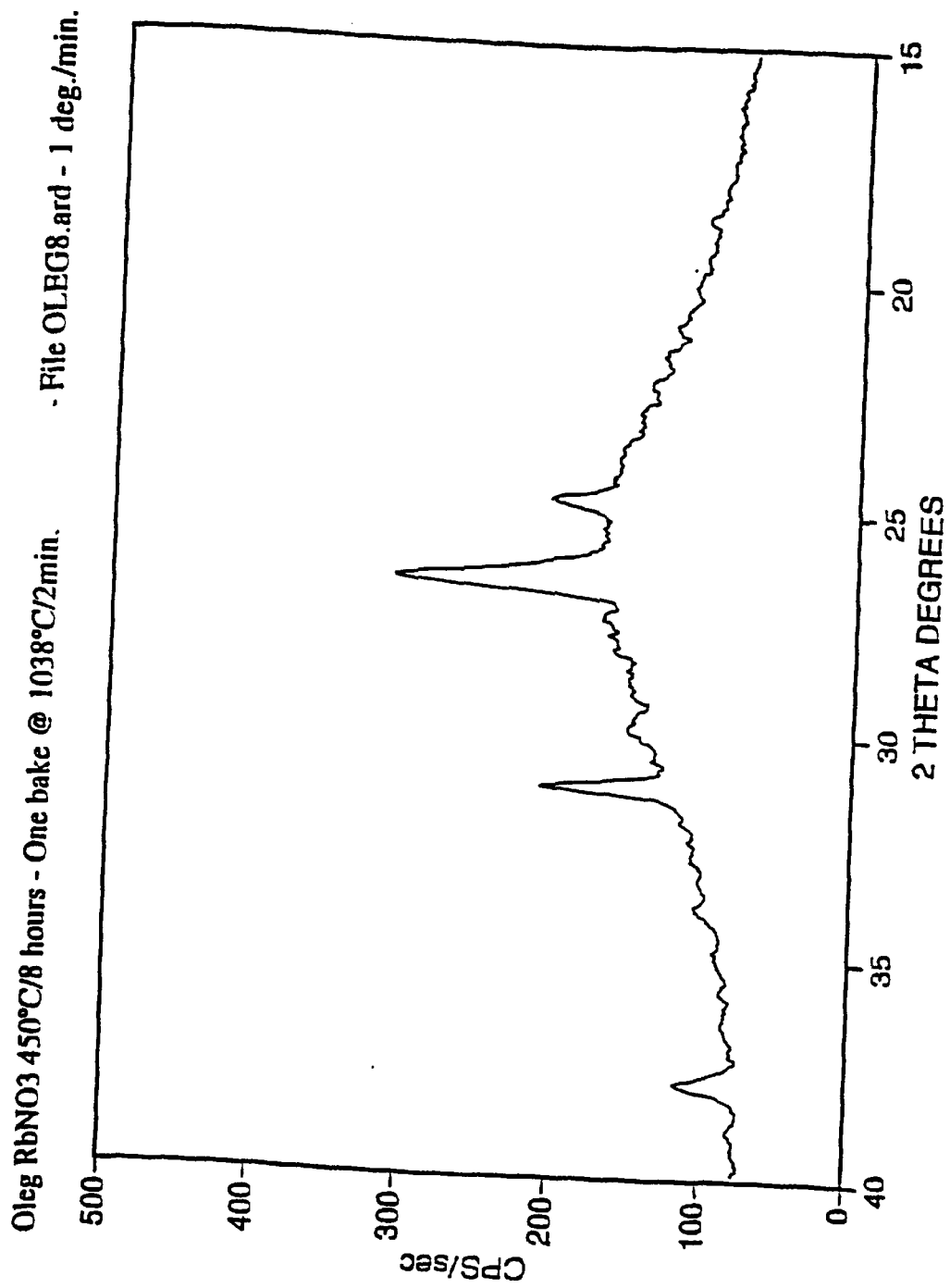
Figure 4C:
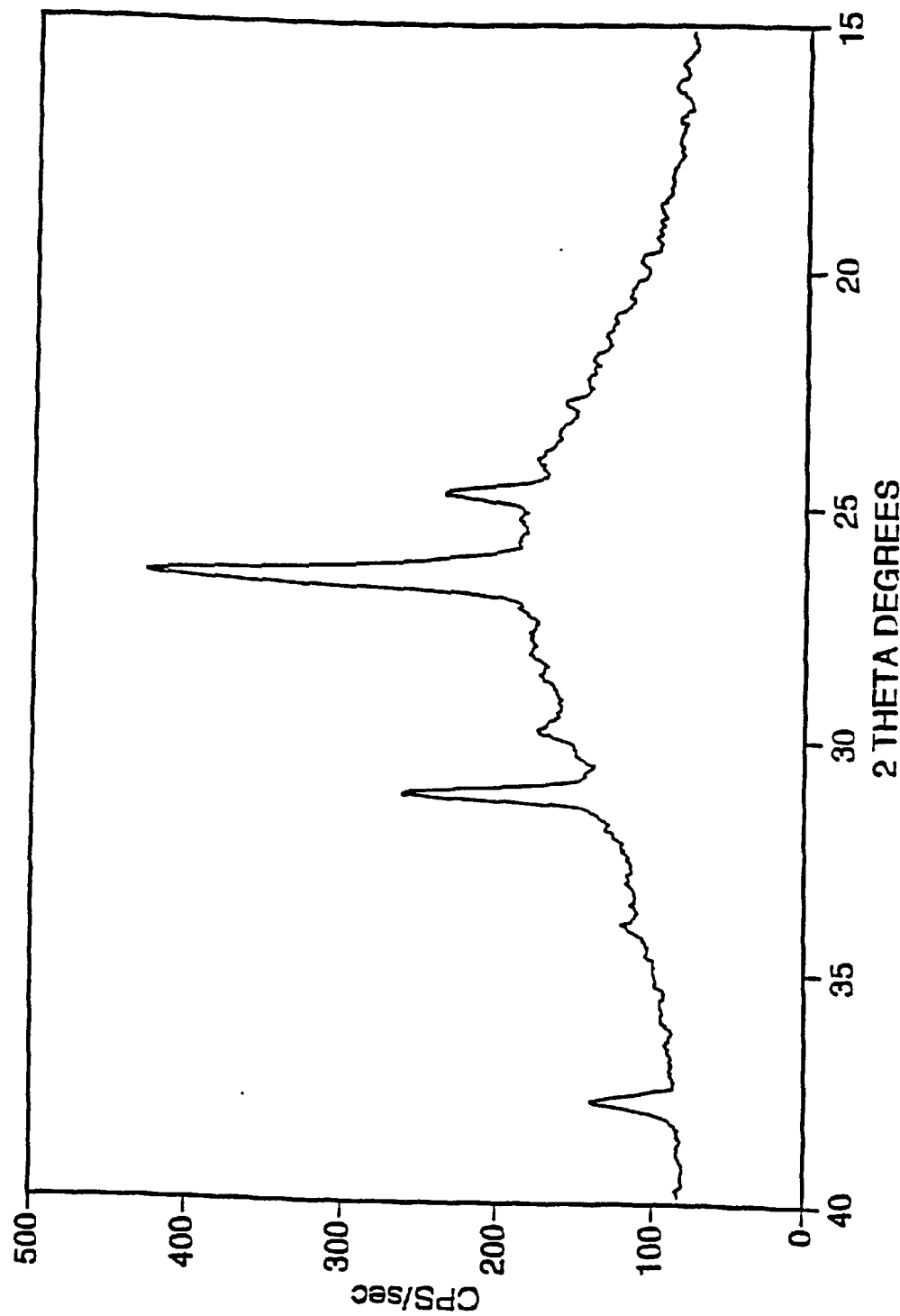
Figure 4D:
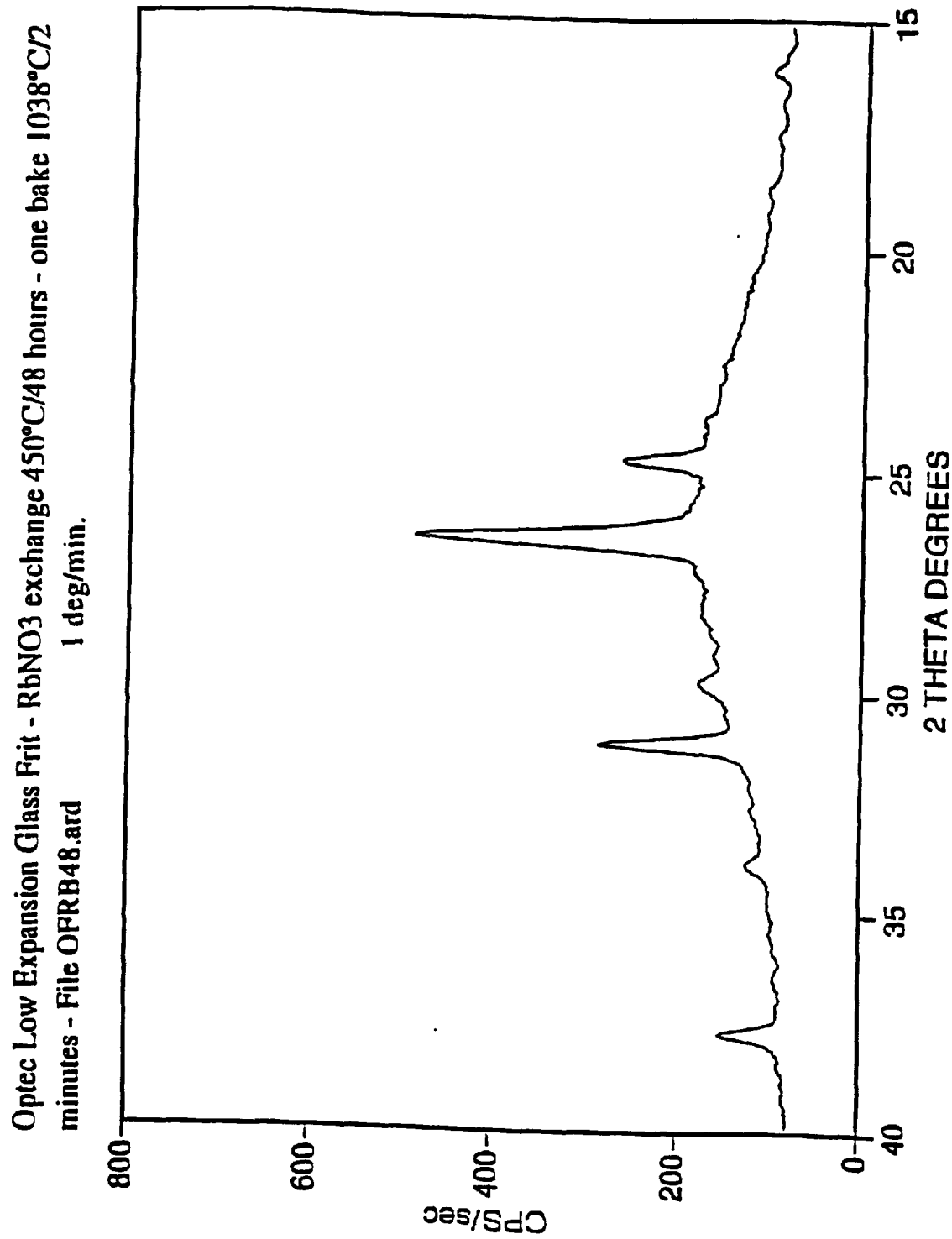

The microstructure of Example 5 is shown in FIG. 6. The average diameter of the cubic leucite crystals was 0.64±0.02 microns and the percent crystallinity was 18.9±2.8%. A small number of larger tetragonal leucite crystals was observed. The number of crystals appeared greater than after ion-exchange for 4 hours.

EXAMPLES 6–8

Figure 7:
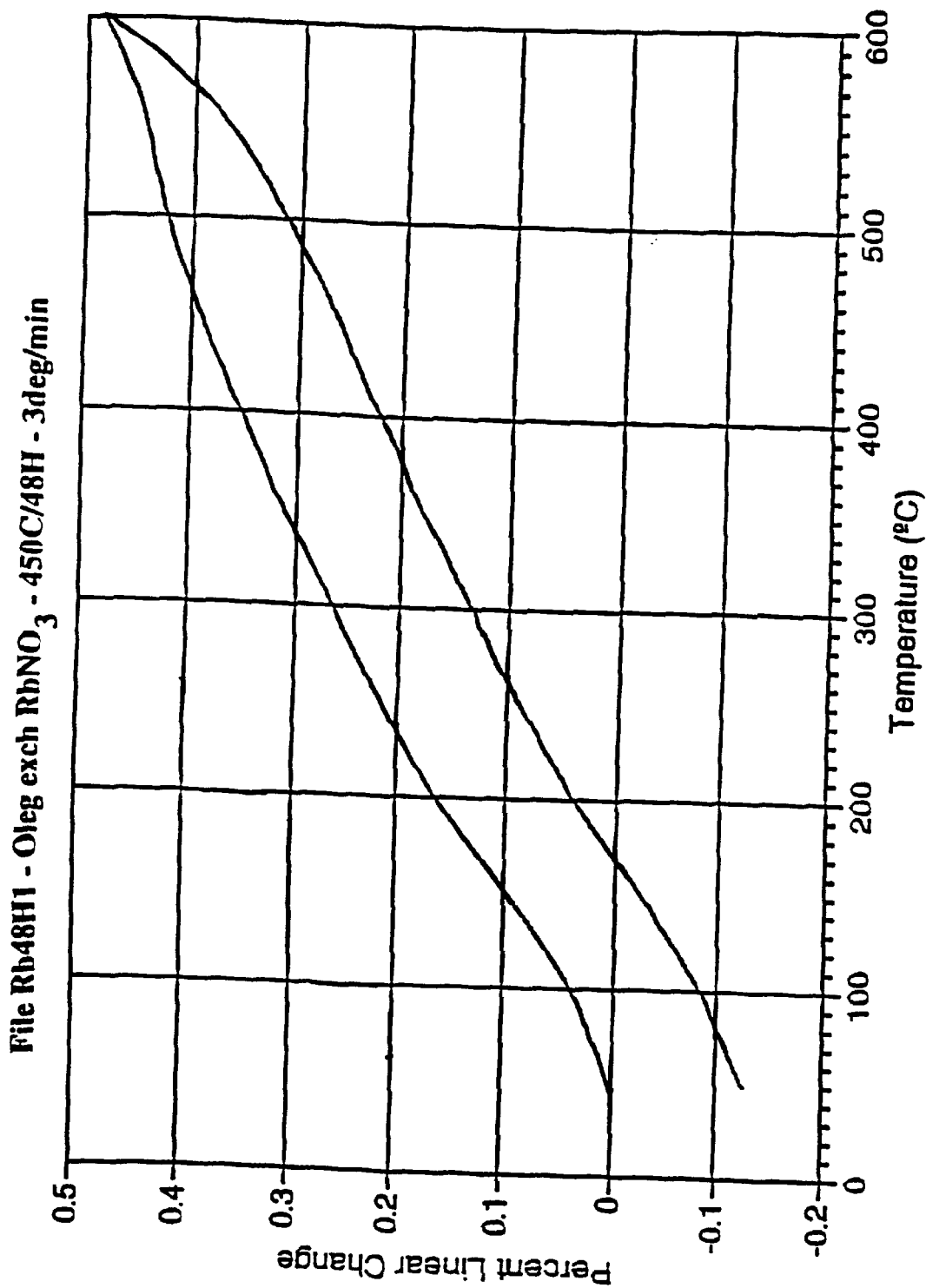
FIG. 7 is a graph depicting a typical thermal expansion curve of the feldspathic porcelain composition of this invention.

The coefficient of thermal expansion was recorded for three specimens (Examples 6–8) prepared by ion-exchange with $RbNO_3$ for 48 hours followed by heating up to 1038° C. and baking at 1038° C. at atmospheric pressure for 2 minutes as described in Example 1. A typical thermal expansion curve is shown in FIG. 7. The mean coefficient of thermal expansion for Examples 6–8 was $8.788 \pm 0.087 \times 10^{-6}/°$ C. when measured at 25° to 550° C.

EXAMPLES 9–14 AND COMPARATIVE EXAMPLE 3

The effect of further heat treatment on the particle size and percent crystallinity of the feldspar porcelain composition was investigated. Glass powder was prepared by ion-exchange with $RbNO_3$ for 48 hours as described previously in Example 1. The specimens (bars) were heated up to 1038° C. and baked at 1038° C. at atmospheric pressure for 2 minutes as described in Example 1 and further heat treated for 4 hours at 800°, 850°, 900°, 950°, or 1038° C. Results are presented in Table 2 below:

TABLE 2

| Example | Further Heat Treatment | Ion-Exchange | % Crystallinity | Average Particle Size ($\mu$m) |
| --- | --- | --- | --- | --- |
| Comparative Example 3 | none | no | N/A (amorphous) | N/A |
| 9 | none | yes | 18.9 ± 2.8 | 0.64 ± 0.02 |
| 10 | 800° C./4 hours | yes | 25.7 ± 15.0 | 0.67 ± 0.05 |
| 11 | 850° C./4 hours | yes | 36.2 ± 5.2 | 0.76 ± 0.06 |
| 12 | 900° C./4 hours | yes | 42.9 ± 1.9 | 1.04 ± 0.16 |
| 13 | 950° C./4 hours | yes | 39.3 ± 5.1 | 1.18 ± 0.06 |
| 14 | 1038° C./4 hours | yes | 37.9 ± 3.8 | 0.77 ± 0.10 |

Figure 8A:
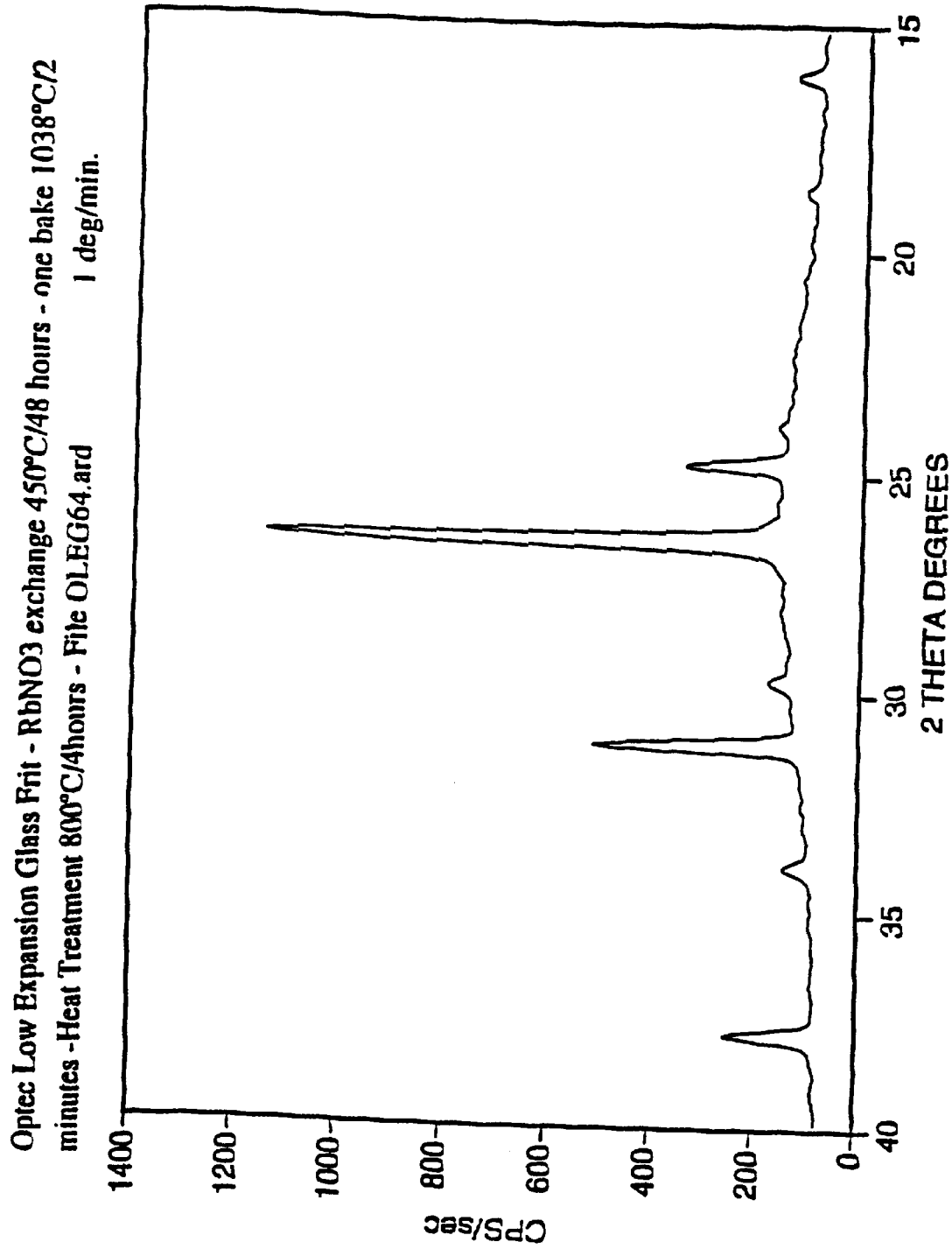
FIGS. 8(a) through 8(e) are x-ray diffraction patterns of various specimens produced by one embodiment of the method of this invention.
Figure 8B:
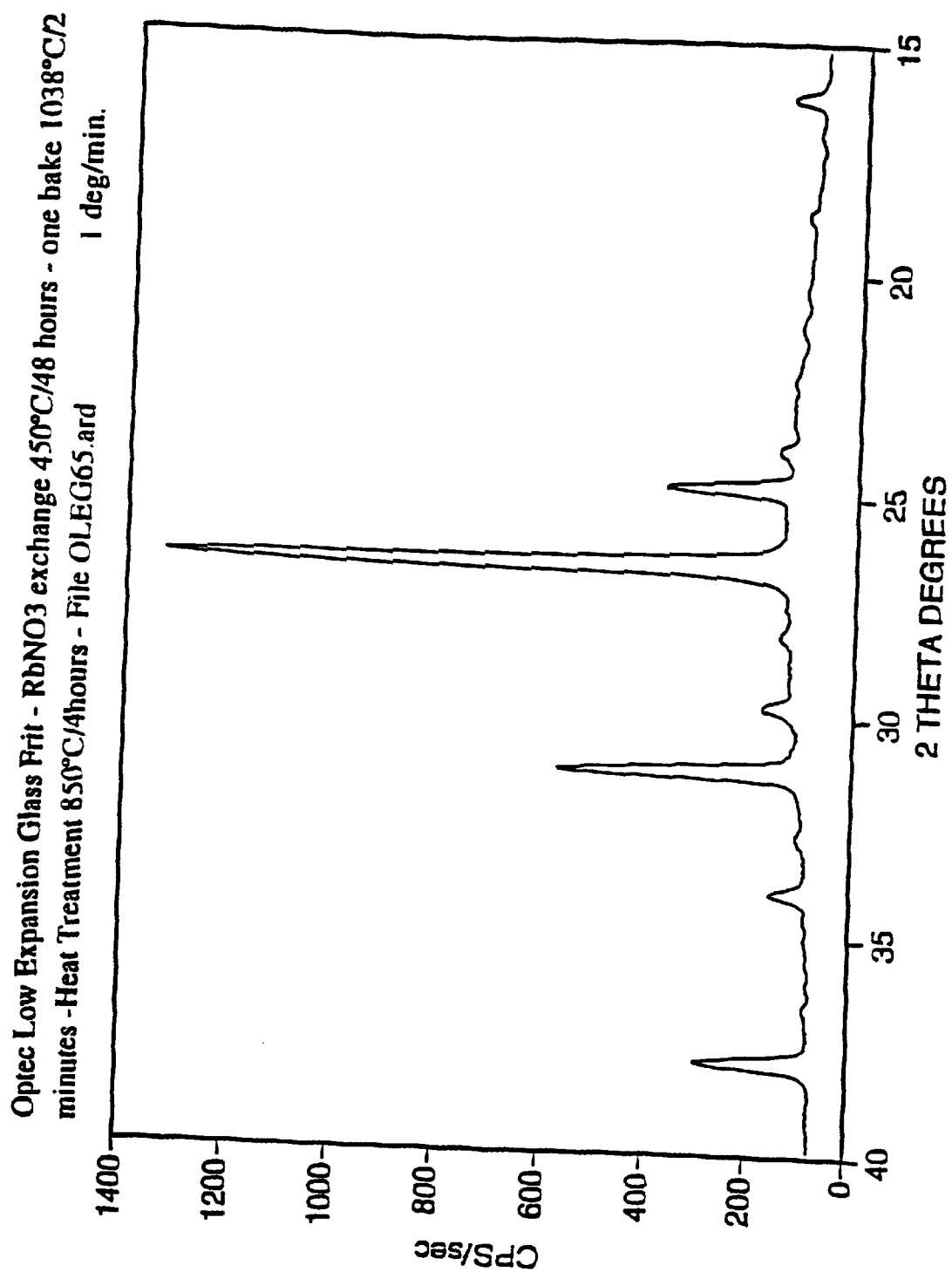
Figure 8C:
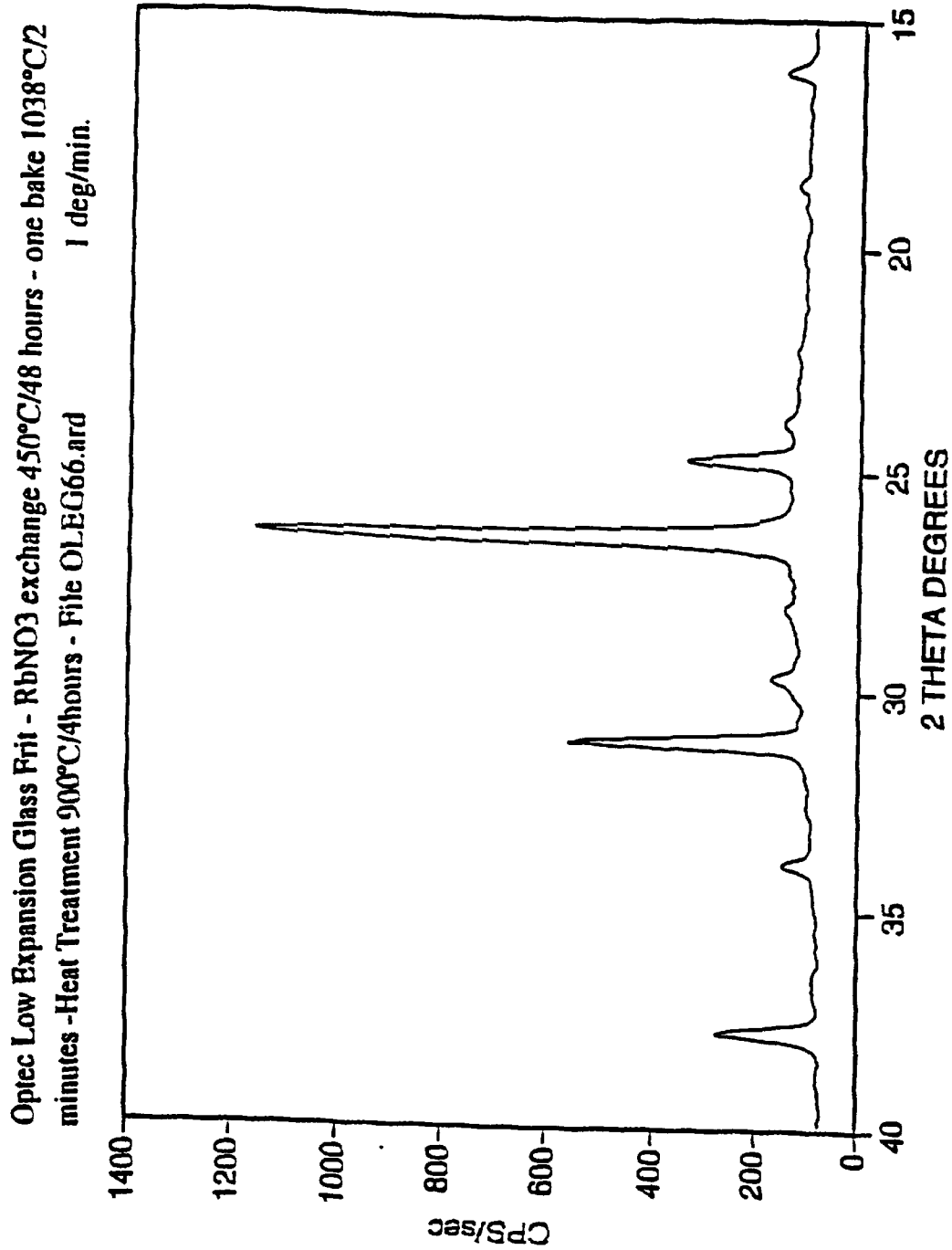
Figure 8D:
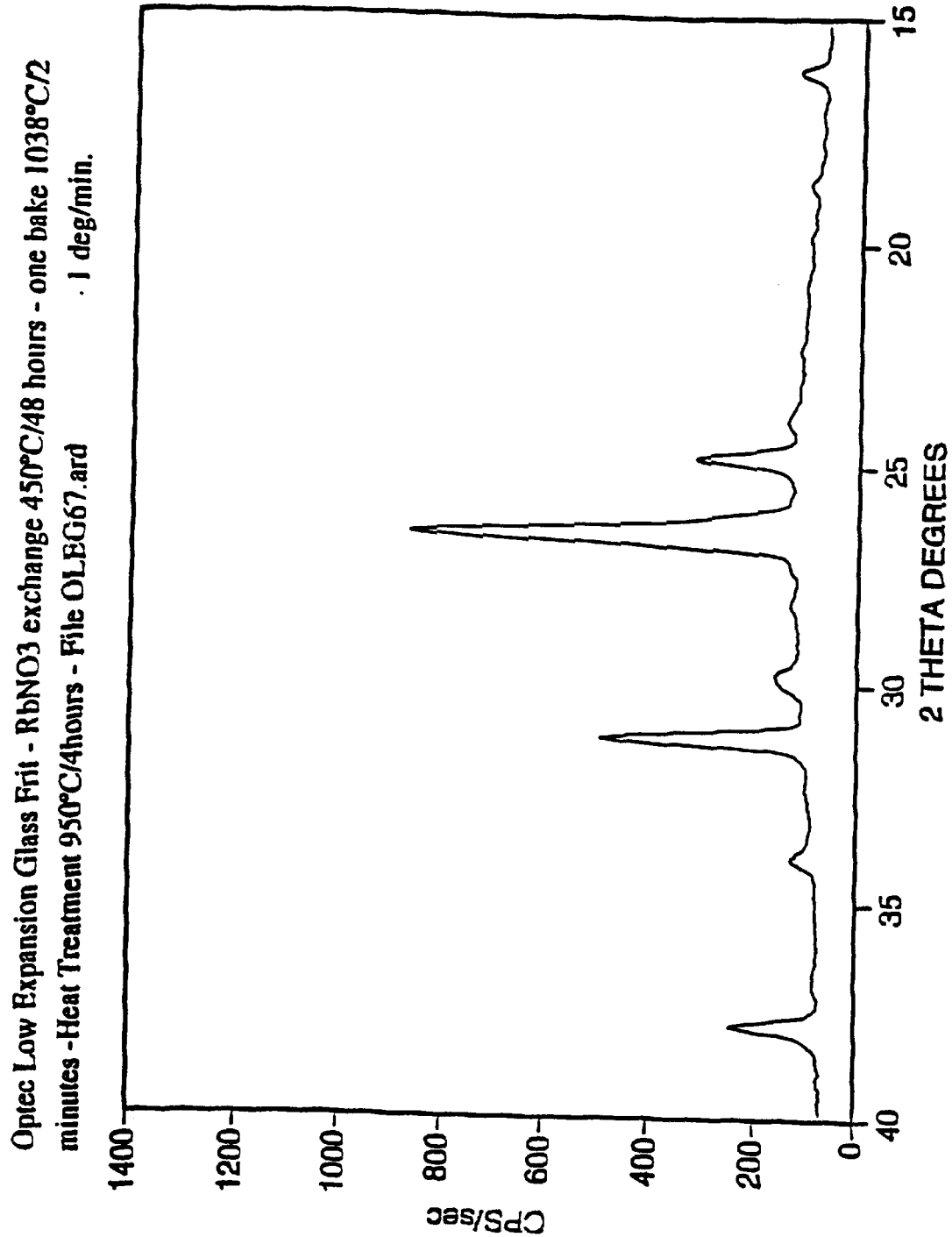
Figure 8E:
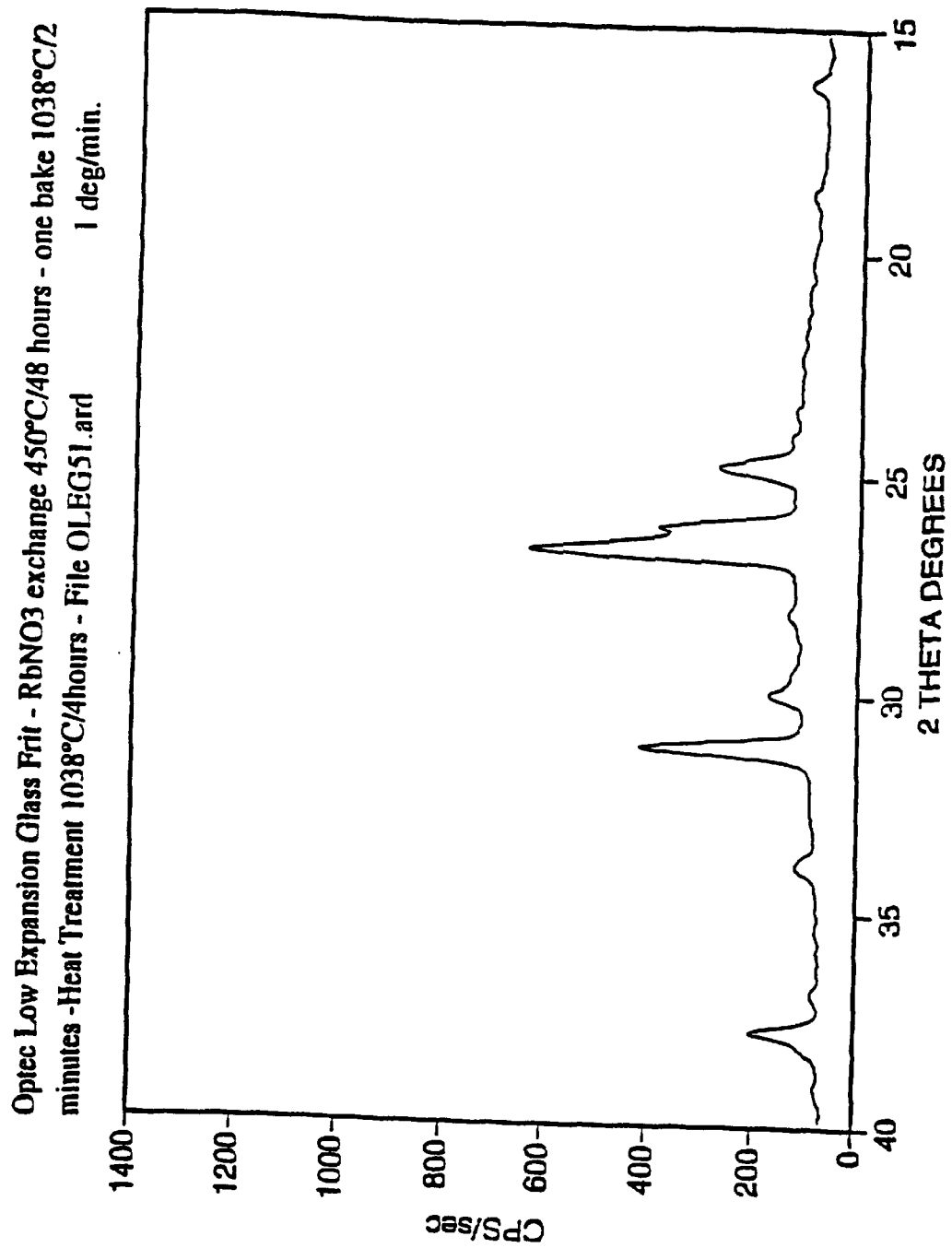
Figure 9A:
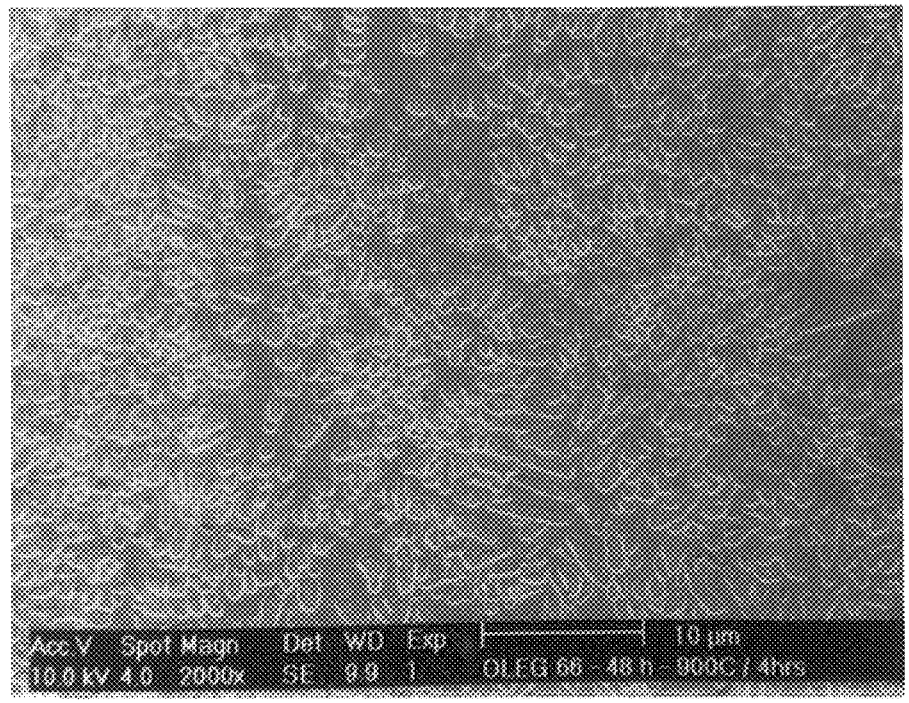
FIGS. 9(a) and (b) and 10(a) and (b) are SEM photomicrographs of certain specimens produced in accordance with one embodiment of the method of this invention, at 2000× and 4000×, respectively.
Figure 9B:
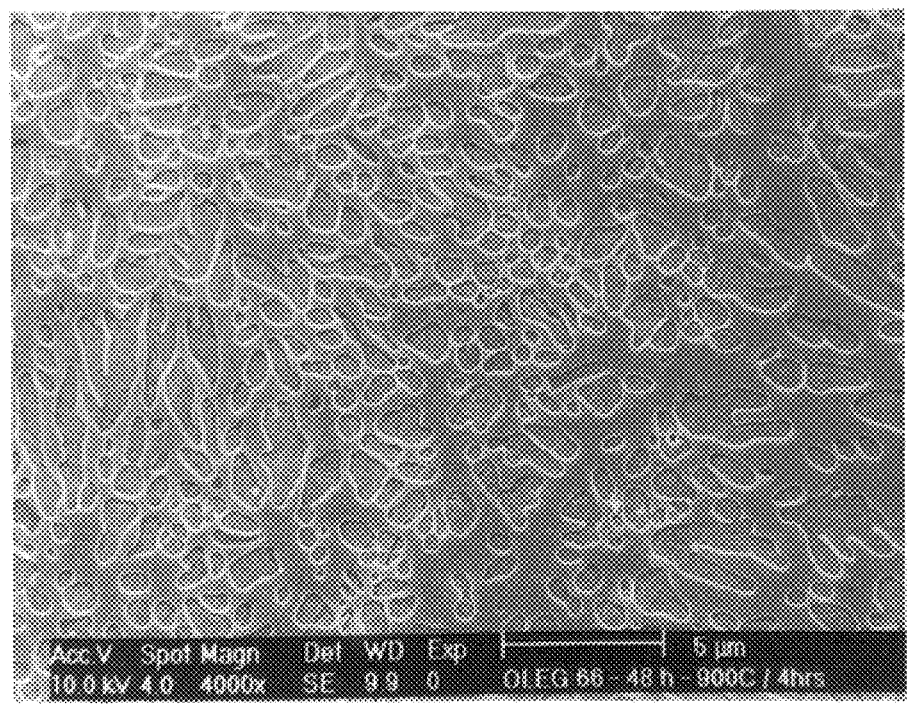
Figure 10:
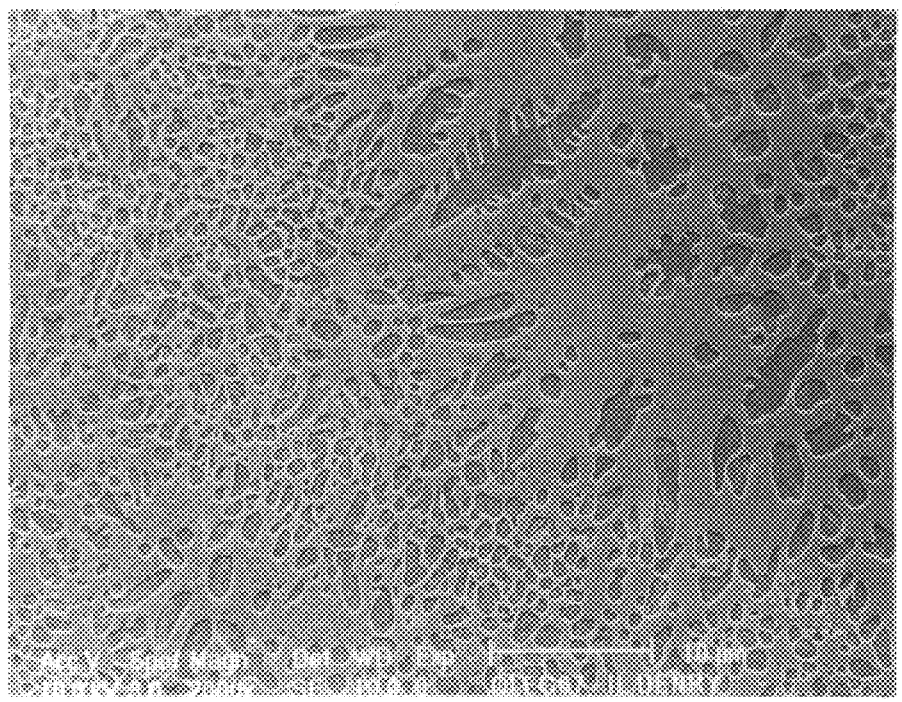
Figure 10:
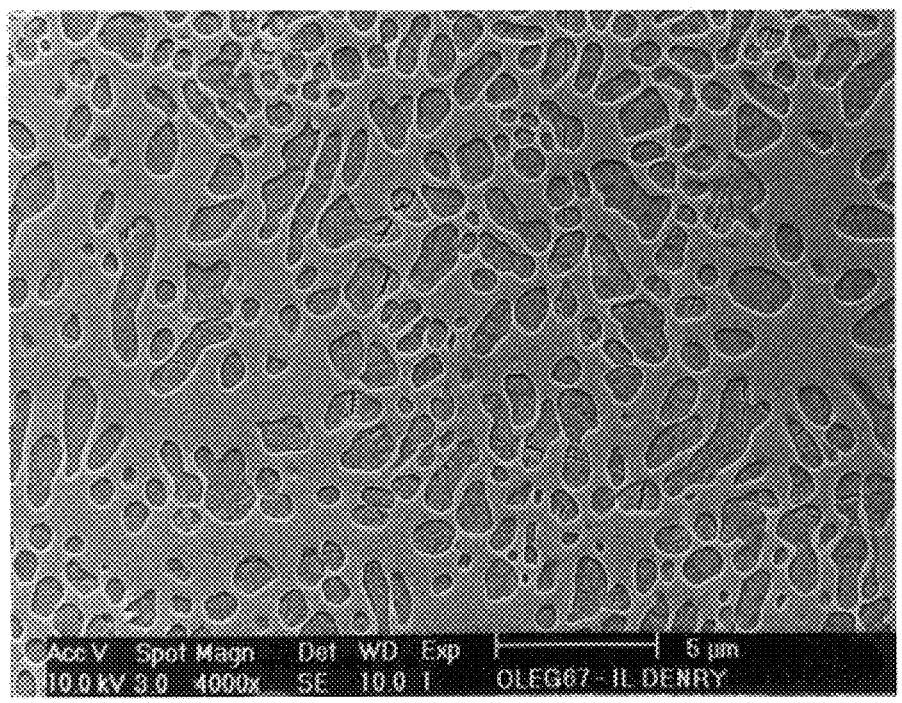

X-ray diffraction showed the presence of cubic leucite as the only crystalline phase for Examples 10–13 (FIGS. 8(a), (b), (c), and (d)). Splitting of some of the diffraction peaks showed the presence of tetragonal rubidium-leucite in Example 14 after treatment at 1038° C. for 4 hours (FIG. 8(e)). SEM examination showed that the average particle size was significantly greater for Example 12 (FIGS. 9(a) and (b)) and Example 13 (FIGS. 10(a) and (b)) than for all other Examples (p<0.0003). Ion-exchange promoted the crystallization of cubic leucite in feldspar glass up to 42.9% by weight with an average particle size of 1.04 $\mu$m.

EXAMPLES 15–18

Figure 11A:
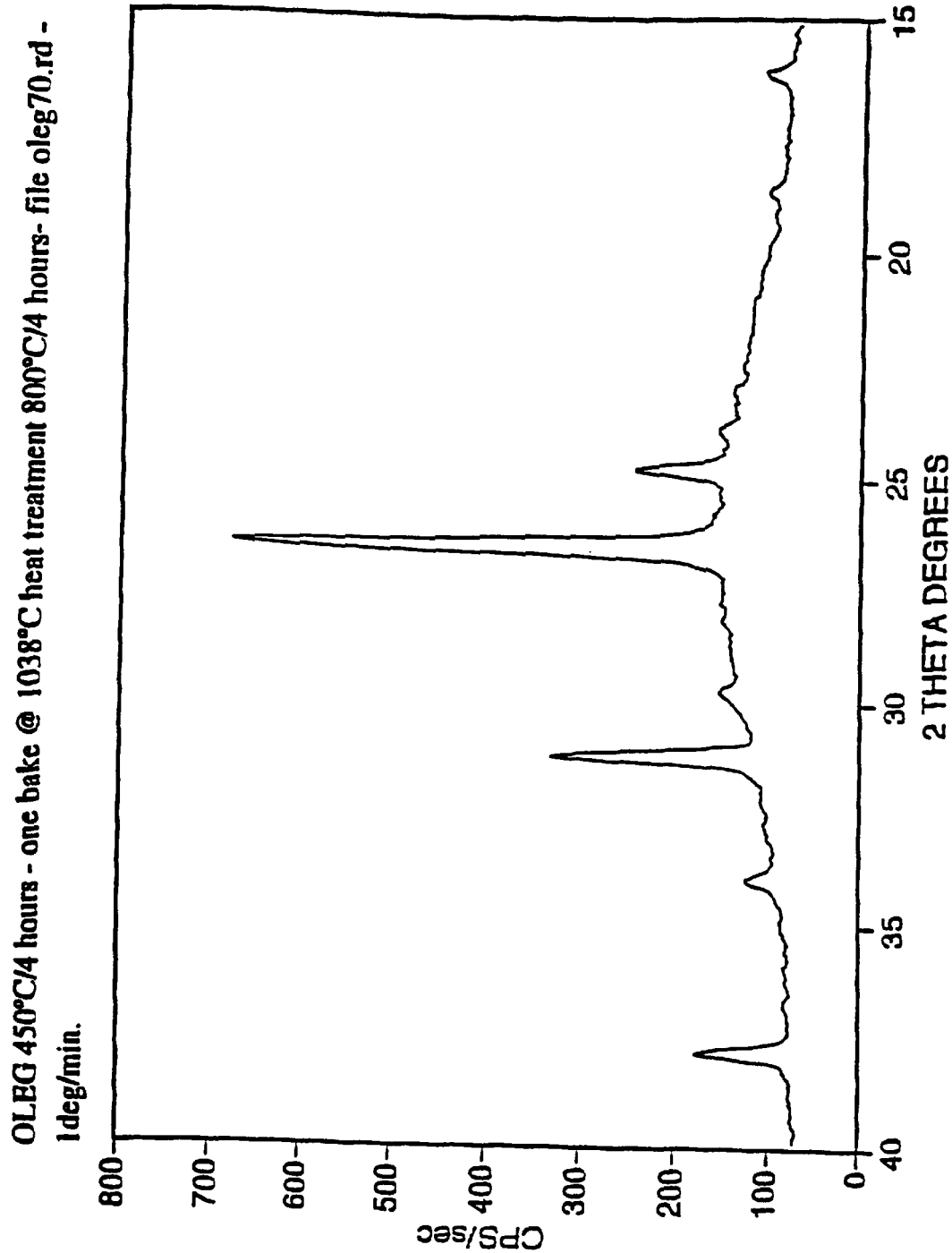
FIGS. 11(a) through 11(d) are x-ray diffraction patterns which demonstrate that the amount of discontinuous crystalline phase increases with the duration of the ion-exchange in combination with an additional heating step.
Figure 11B:
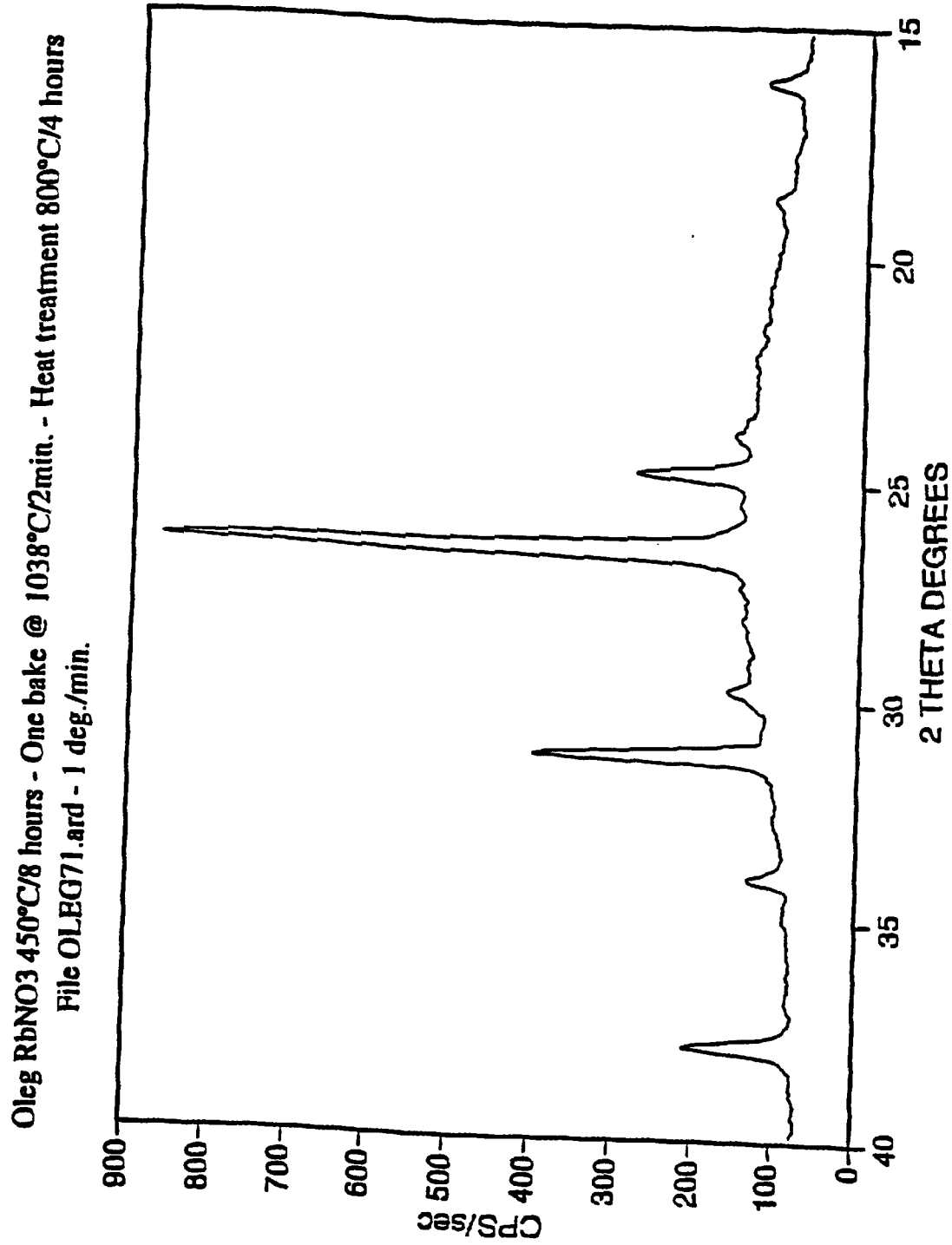
Figure 11C:
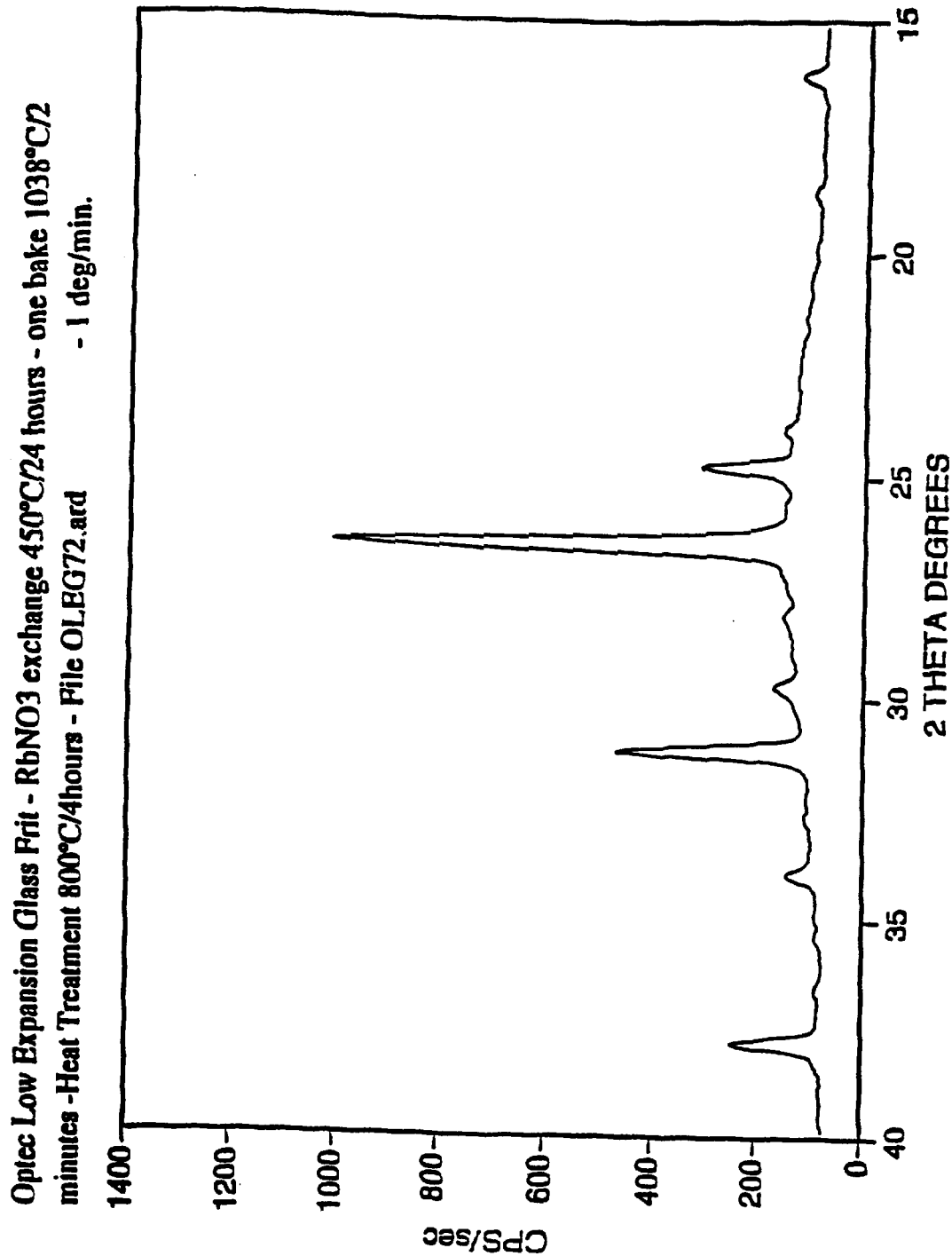
Figure 11D:
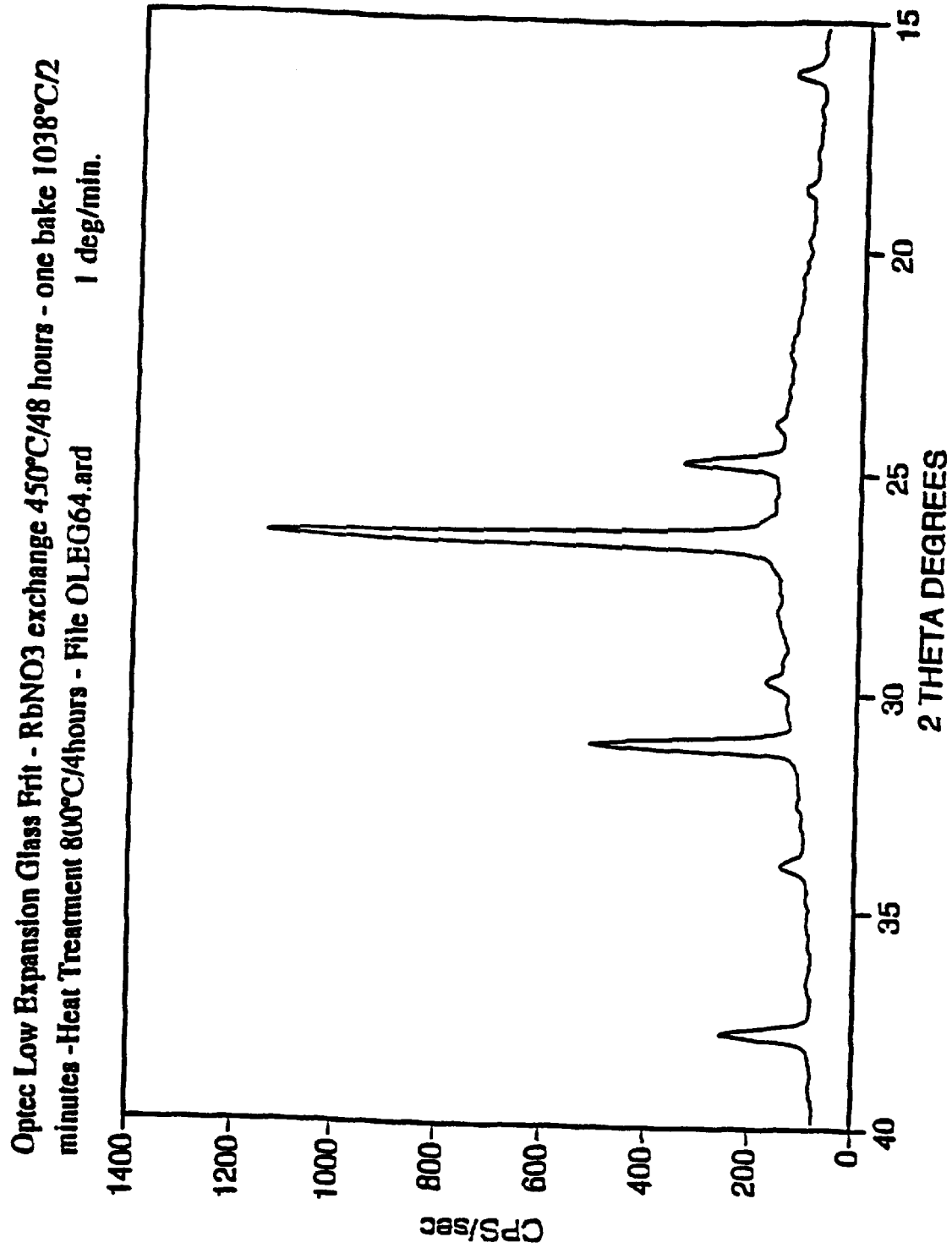
Figures 12A, 12B, 12C, 12D, 12E, 12F:
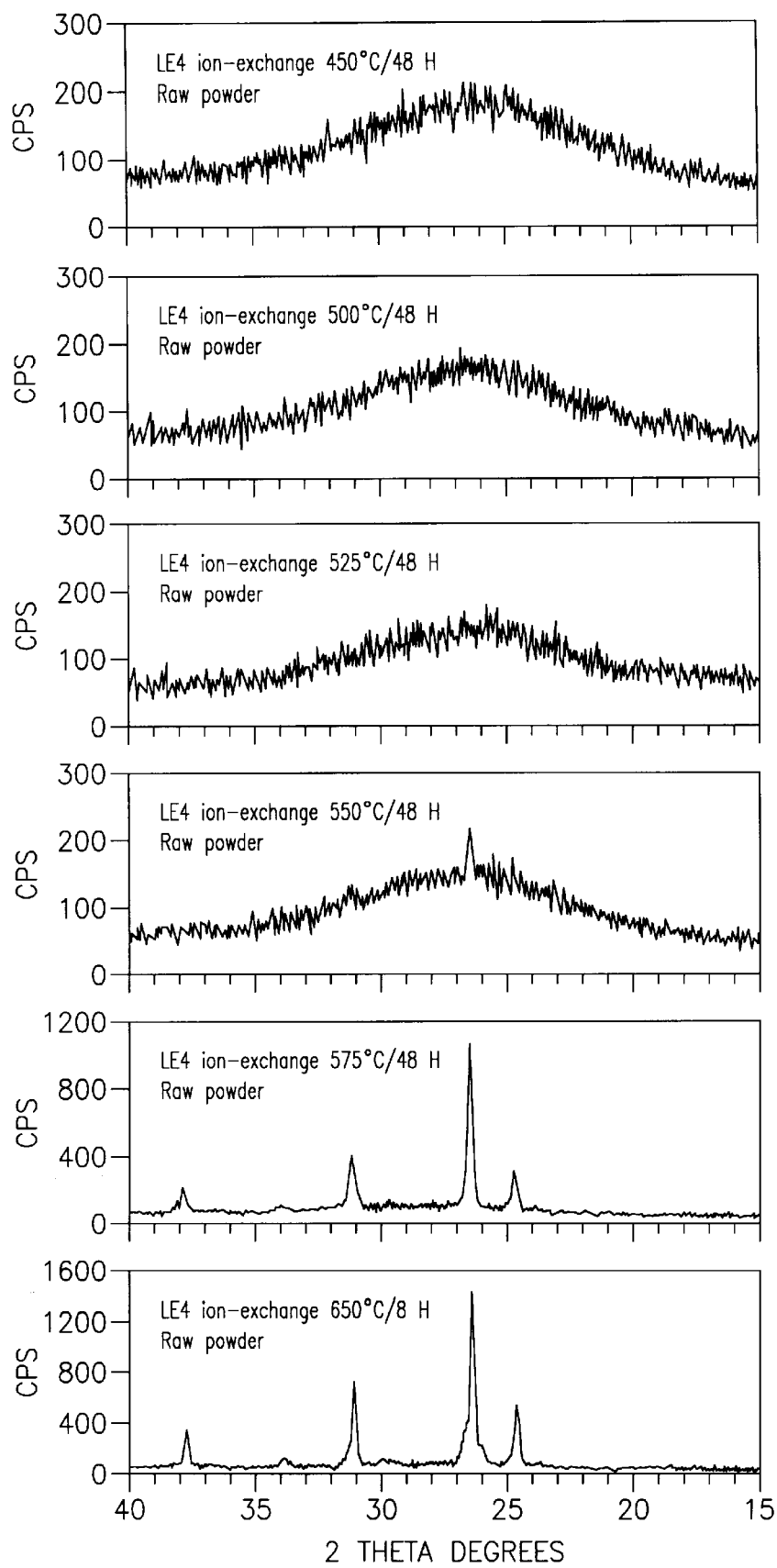
FIGS. 12(a) through 12(f) are x-ray diffraction patterns of the alkali silicate powder after ion-exchange at various temperatures in accordance with another embodiment of the present invention.
Figure 13A:
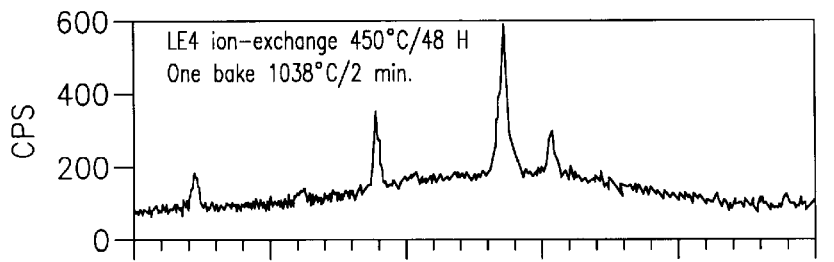
FIGS. 13(a) through 13(f) are x-ray diffraction patterns of ceramic specimens made from ion-exchanged powders after one bake.
Figure 13B:
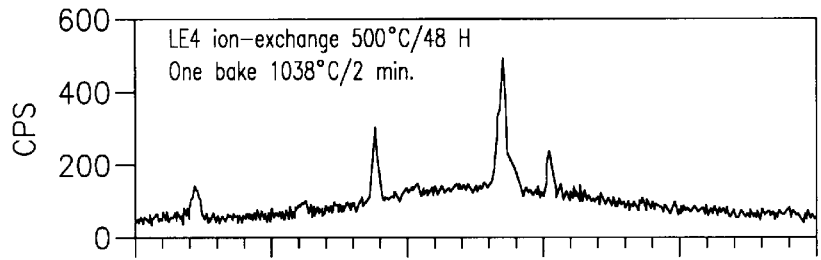
Figure 13C:
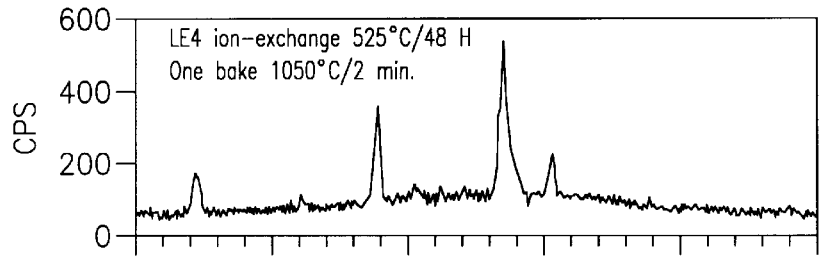
Figure 13D:
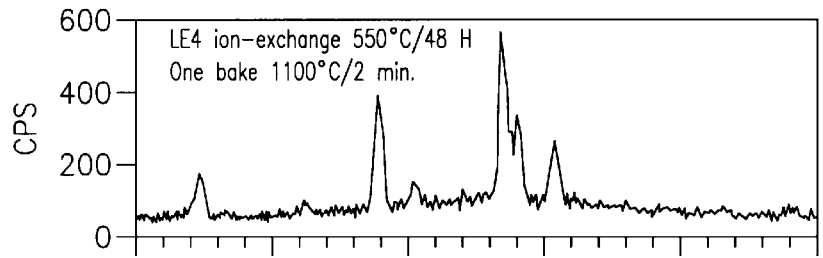
Figure 13E:
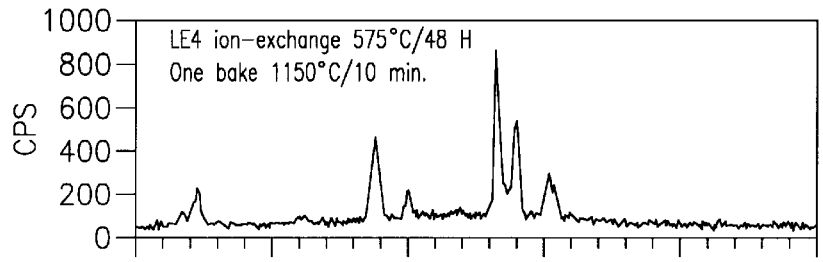
Figure 13F:
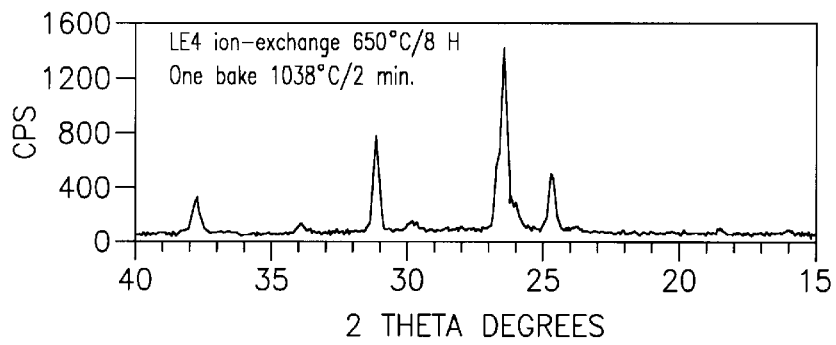
Figure 14:
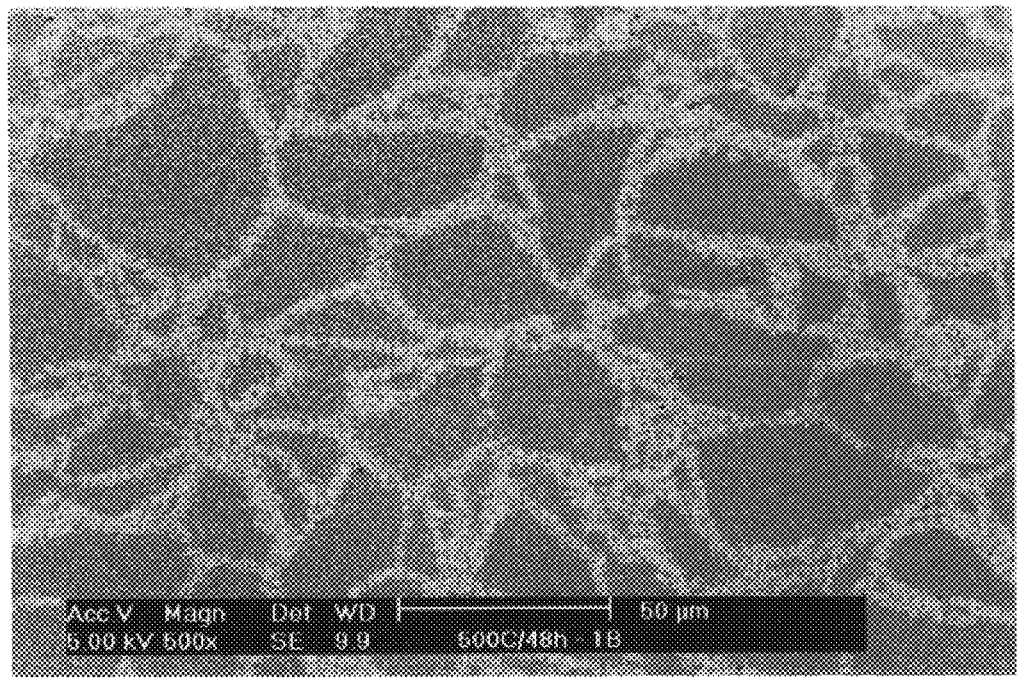
FIGS. 14(a) through 14(d) are microphotographs illustrating the development of cubic leucite crystals with increasing temperature of the ion-exchange treatment.
Figure 14:
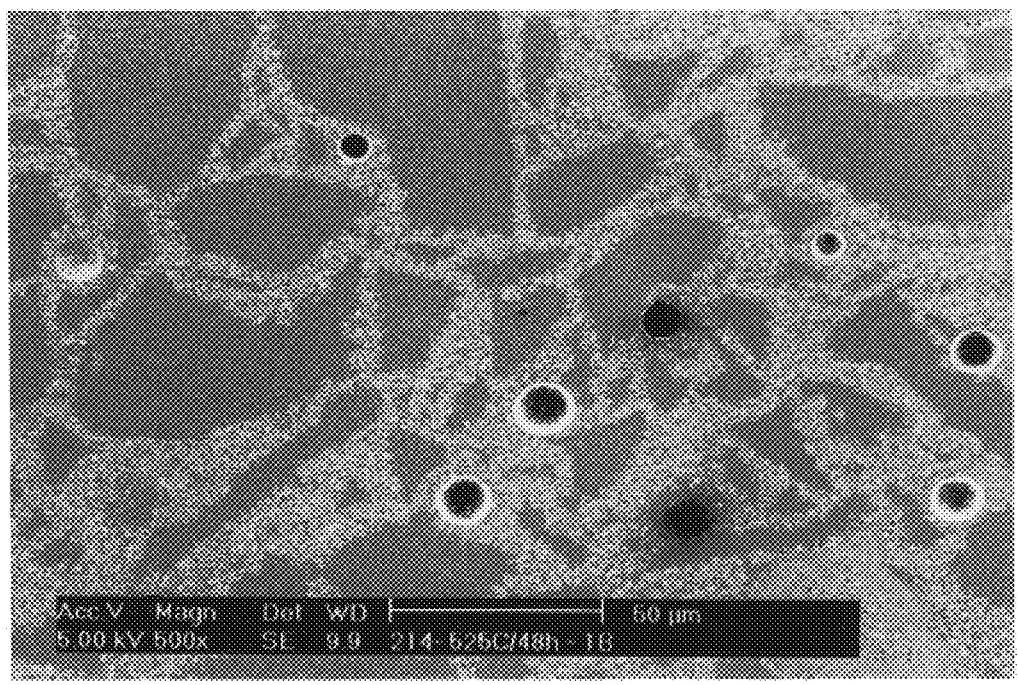
Figure 14:
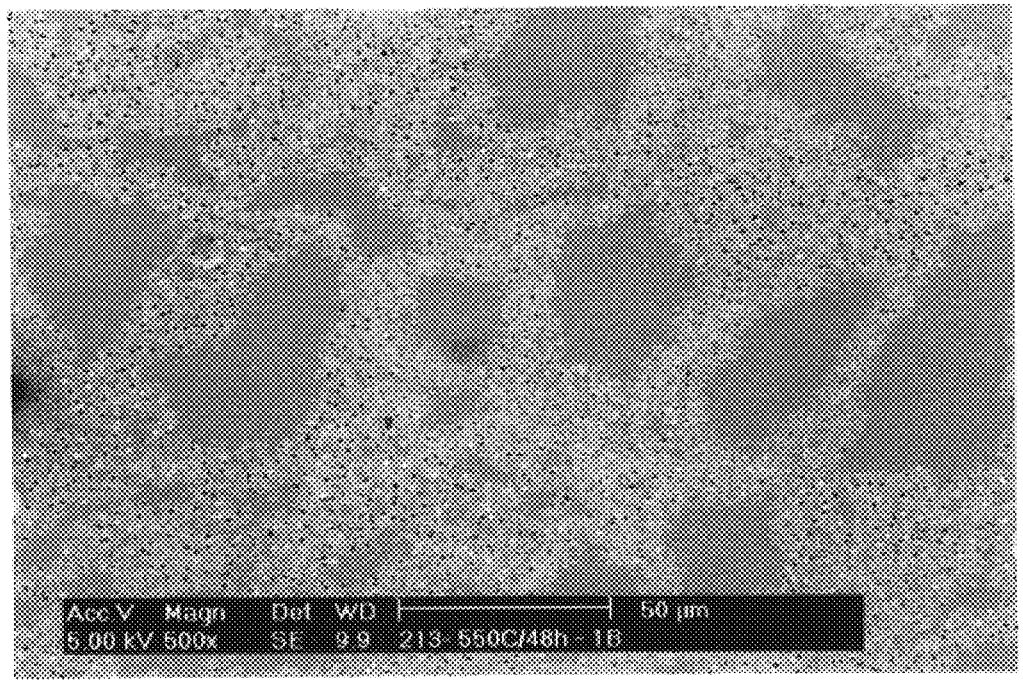
Figure 14:
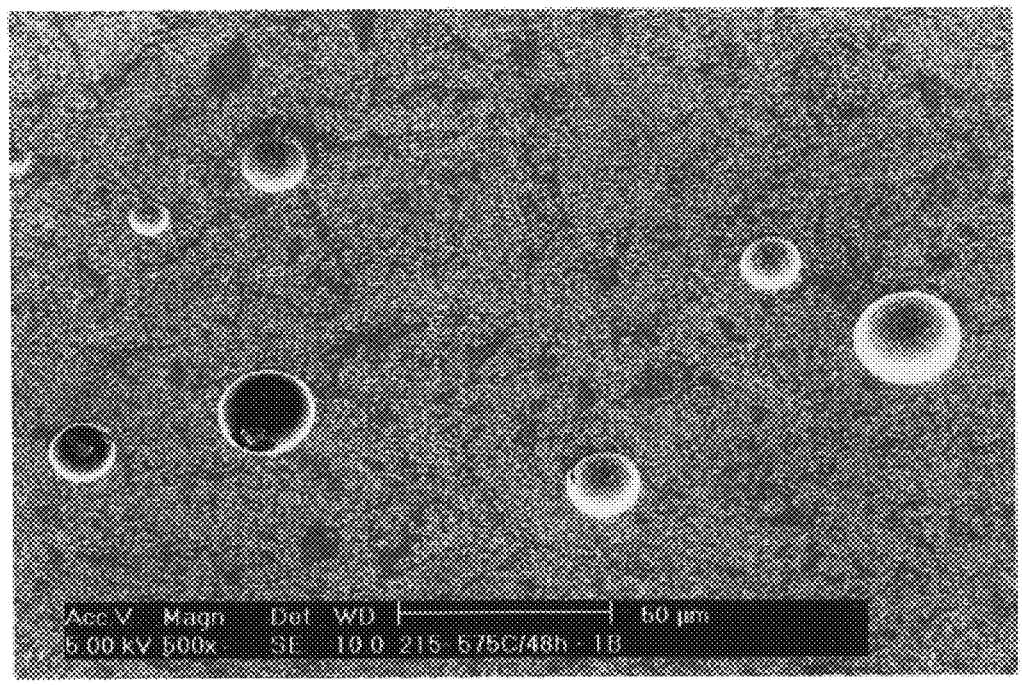

The effect of the ion-exchange treatment time on percent crystallinity of specimens that were further heat treated was evaluated as follows. Four separate mixtures of powders as described in Example 1 were ion exchanged at 450° C. for 4, 8, 24 and 48 hours (Examples 15–18, respectively) to effect an exchange of predominantly sodium and a lesser amount of potassium ions derived from the feldspar glass with rubidium ions derived from rubidium nitrate. The resulting ion-exchanged powdered materials were then individually rinsed and dried at 150° C. for 2 hours. The resulting amorphous materials were individually mixed into slurries using dental porcelain build-up liquid (Universal Porcelain™ build-up liquid, Jeneric/Pentron, Inc., Wallingford, Conn.) and manually condensed into a split mold to form bars (4×8×25 mm). The bars were heated at a heat-up rate of 55° C. per minute under vacuum in a porcelain oven starting at 600° C. and rising to 1038° C., at which temperature the vacuum was released. The bars were held at 1038° C. at atmospheric pressure for 2 minutes. The bars were further heat treated at 800° C. for 4 hours. X-ray powder diffraction showed that the amount of crystalline phase increased with the duration of the ion-exchange treatment (FIGS. 11(a), (b), (c) and (d)).

EXAMPLE 19

The following example illustrates the uptake of rubidium in the cubic potassium leucite network after ion-exchange of a feldspathic glass with rubidium nitrate.

The crystallization of cubic leucite in feldspar glass is promoted by low temperature ion-exchange of the feldspar glass powder with rubidium nitrate. It is postulated that rubidium acts as a nucleating agent and is later included in the cubic potassium leucite network. Rubidium ions being larger than potassium ions, the replacement of part of the potassium ions for rubidium ions in the leucite structure leads to an increase in the lattice parameter with little change in the c lattice parameter. Direct evidence of the presence of rubidium in the cubic potassium leucite network can therefore be obtained via measurement of the lattice parameters of cubic leucite. (Martin and Lagache (1975)) A linear relationship has been shown to exist between the amount of rubidium or cesium in the tetragonal leucite network and the cell volume.

The lattice parameter equals 13.43 Å for cubic potassium leucite (Hermansson and Carlsson (1978)) and 13.60 Å for cubic rubidium leucite (Kosorukov and Nadel (1985)). The lattice parameter variation corresponding to the replacement of 100% potassium ions with rubidium ions is 0.17 Å.

A summary of the lattice parameter of cubic leucite in the low expansion feldspar glass of Example 1 obtained by ion-exchange with rubidium, along with the calculation of the amount of potassium exchanged for rubidium is presented in Table 3.

TABLE 3

Lattice parameter measurements and calculations for the various materials.

| Material | | Lattice parameter a (Å) | shift | Amount K exchanged for Rb (%) |
|---|---|---|---|---|
| Rb ion-exchange 450° C./8 hours | A | 13.452 | 0.022 | 12.94 |
| Rb ion-exchange 450° C./48 hours | B | 13.464 | 0.034 | 20.00 |
| Rb ion-exchange 650° C./48 hours | C | 13.473 | 0.043 | 25.29 |
| Rb ion-exchange 450° C./48 hours One bake + heat tx 1038° C./4 hours | D | 13.447 | 0.017 | 10.00 |
| Rb ion-exchange 650° C./48 hours One bake 1038° C./2 min. | E | 13.447 | 0.017 | 10.00 |
| 1693 + 15% LE Glass of Example 1 Rb ion-exchange 500° C./48 hours – One bake 1100° C./2 min – Heat tx 900° C./4 hours | F | 13.477 | 0.047 | 27.76 |

It can be seen that the amount of rubidium incorporated in the potassium leucite network increases with the duration of the ion-exchange treatment as well as the temperature of the ion-exchange treatment. The crystalline phase formed in all ion-exchanged feldspar glasses is cubic leucite with the following formula:

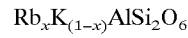

Knowing the amount of potassium replaced with rubidium in the leucite network, it is possible to calculate the weight percentage of rubidium in the network. For example, in material D, 10% of the potassium sites are occupied by rubidium ions; this translates into 3.8 weight % rubidium in leucite. Material D contains 37.9% cubic Rb/K leucite, which results into 1.44% rubidium in the ceramic material.

When the ceramic is further heat treated at 1038° C. for four hours, the amount of rubidium occupying the potassium sites in the leucite network decreases while a second phase appears in the material. This second phase is tetragonal rubidium leucite with almost 100% of the potassium sites occupied by rubidium ions. This result can be explained by the fact that high temperature or longer heat treatments favor the diffusion of rubidium ions more completely into the cubic potassium leucite network.

EXAMPLE 20

The low expansion feldspar glass of Example 1 was mixed in equal proportions with rubidium nitrate and heat treated for 48 hours at 450°, 500°, 525°, 550°, 575° C. One mix was heat treated at 650° C. for 8 hours. The powders were rinsed to eliminate rubidium nitrate and dried at 150° C. for 2 hours. X-ray diffraction analyses were performed on the powders after drying. Ceramic bars (25×6×8 mm) were formed using a split mold and baked at temperatures ranging from 1038° to 1150° C. for times ranging from 2 and 10 minutes (Table 4).

TABLE 4

Firing conditions for the various materials.

| Material | Heat Treatment | Firing Conditions |
|---|---|---|
| A | 450° C./48 hours | 1038° C./2 min. |
| B | 500° C./48 hours | 1038° C./2 min. |
| C | 525° C./48 hours | 1050° C./2 min. |
| D | 550° C./48 hours | 1100° C./2 min. |
| E | 575° C./48 hours | 1150° C./2 min. |
| F | 650° C./8 hours | 1038° C./2 min. |

The thermal expansion and contraction between 25° and 600° C. was recorded on bars at a heating rate of 3° C. per minute and a cooling rate of 1° C. per minute. Powdered specimens were analyzed by x-ray diffraction. Scanning electron microscopy was performed on polished specimens. Four micrographs per specimen were used to evaluate the percent crystallinity.

X-ray diffraction (XRD) analyses on the raw powders (FIGS. 12(a)–12(f)) showed that the specimens were amorphous (glassy matrix only) after ion-exchange at 450°, 500° and 525° C. Cubic leucite was present in small amount in the powder exchanged at 550° C. and large amount in the powder exchanged at 575° C. The powder exchanged at 650° C. for 8 hours contained a very large amount of cubic leucite ($Rb_xK_{(1-x)}Si_2O_6$) with a small amount of tetragonal rubidium leucite. Calculations from the lattice parameters measurements showed that 25.29% of the potassium sites in the cubic leucite network were occupied by rubidium. The results from x-ray diffraction analyses after one bake are summarized in Table 5 and FIGS. 13(a)–13(f).

TABLE 5

Effect of ion-exchange temperature on
the crystallization of LE4 feldspar glass.

| Material | Heat Treatment | XRD Raw Powder | XRD One Bake |
|---|---|---|---|
| A | 450° C./48 hours | glassy phase | cubic leucite (+) |
| B | 500° C./48 hours | glassy phase | cubic leucite (+) |
| C | 525° C./48 hours | glassy phase | cubic leucite (+) |
| D | 550° C./48 hours | cubic leucite (+) | cubic leucite tetragonal Rb-leucite |
| E | 575° C./48 hours | cubic leucite (+++) | cubic leucite tetragonal Rb-leucite |
| F | 650° C./8 hours | cubic leucite (++++) tetragonal Rb-leucite | cubic leucite (++++) tetragonal Rb-leucite (+) |

The results of the thermal expansion measurements are presented in Table 6.

TABLE 6

Differential coefficient of thermal
contraction for the various materials tested.

| Material | Heat Treatment | DCC (550–50° C.) ($\times 10^{-6}/°$ C.) |
|---|---|---|
| Control | No treatment | 8.076 ± 0.151 |
| A | 450° C./48 hours | 8.788 ± 0.140 |
| B | 500° C./48 hours | 9.676 ± 0.036 |
| C | 525° C./48 hours | 12.491 ± 0.010 |
| D | 550° C./48 hours | 13.163 |
| E | 575° C./48 hours | 18.374 ± 0.180* |
| F | 650° C./8 hours | — |

*relates more to DCC of the glassy matrix

It is clear from the microphotographs (FIGS. 14(a)–14(d)) that the temperature of the ion-exchange treatment promotes the development of cubic leucite crystals in the glass composition.

Figure 15:
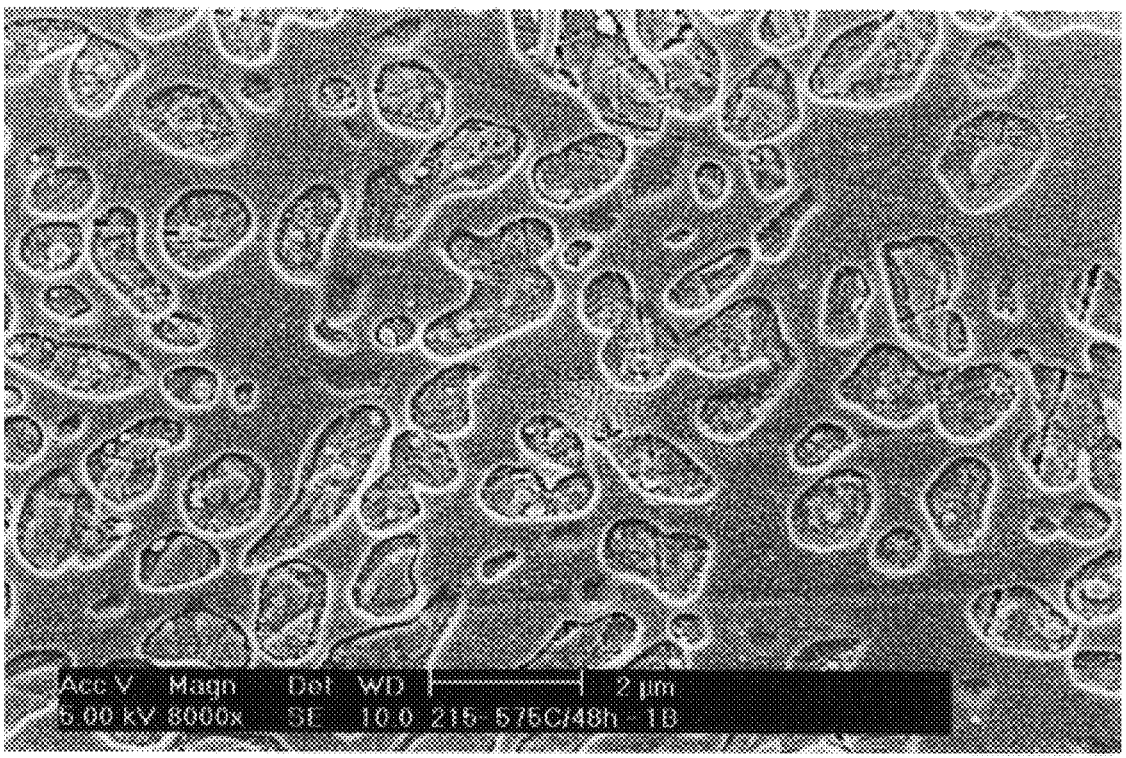
FIG. 15 is a microphotograph of a ceramic specimen made from an alkali aluminosilicate powder after ion-exchange at 575° C. for 48 hours.

Higher magnification confirmed the small size of the crystals (around 2 microns) present in the material exchanged at 575° C. for 48 hours (FIG. 15). The results from dilatometric analyses showed that the thermal expansion of the ceramics increased with the ion-exchange temperature. However, cubic leucite has a very low thermal expansion coefficient (around $3 \times 10^{-6}/°$ C.) between 625° and 900° C. Therefore, an increase in the amount of cubic leucite in the ceramic is unlikely to lead to an increase in the thermal expansion coefficient. One hypothesis to explain this phenomenon would be that at higher temperatures of ion-exchange, the glassy matrix is depleted in alkali ions such as sodium and potassium by the ion-exchange process, resulting in an increase in the coefficient of thermal expansion of the material.

Further variations and modifications of the present invention will become apparent to those skilled in the art from the foregoing and are intended to be encompassed by the claims appended hereto.

What is claimed is:

1. A feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}/°$ C. in the temperature range of 50 to 500° C. and wherein the cubic leucite possesses an average diameter ranging from about 0.5 to about 10 microns.

2. A feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}/°$ C. in the temperature range of 50 to 500° C. and wherein the cubic leucite possesses an average diameter ranging from about 1 to about 4 microns.

3. A feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}/°$ C. in the temperature range of 50 to 500° C. and wherein the discontinuous crystalline phase comprises from about 5 to about 65 weight percent of the composition.

4. A feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}/°$ C. in the temperature range of 50 to 500° C. and further comprising at least one additive selected from the group consisting of an opacifying agent, pigment and fluorescing agent.

5. A feldspathic porcelain composition comprising a continuous glassy matrix phase and a discontinuous, substantially uniformly dispersed crystalline phase which comprises rubidium-stabilized cubic leucite.

6. The composition of claim 5 wherein the rubidium-stabilized cubic leucite possesses an average diameter ranging from about 0.5 to about 10 microns.

7. The composition of claim 5 wherein the rubidium-stabilized cubic leucite possesses an average diameter ranging from about 1 to about 4 microns.

8. The composition of claim 5 wherein the discontinuous crystalline phase comprises from about 5 to about 65 weight percent of the composition.

9. The composition of claim 5 wherein rubidium represents from about 0.19 to about 6.7 weight percent of the composition.

10. The composition of claim 5 further comprising at least one additive selected from the group consisting of an opacifying agent, pigment and fluorescing agent.

11. A method of making a feldspathic porcelain composition which comprises the steps of providing an alkali aluminosilicate powder comprising a feldslpathic glass frit comprising $SiO_2$, $Al_2O_3$, $K_2O$ and $Na_2O$ and at least one metal salt of rubidium, cesium, calcium, strontium or thallium; heating the powder to effect an exchange of alkali cations with metal cations derived from said metal salt to provide a feldspathic porcelain composition which comprises a continuous glassy matrix phase and a discontinuous crystalline phase comprising cubic leucite.

12. The method of claim 11 further comprising the step of reheating the feldspathic porcelain composition at a temperature in the range of about 600° to about 1100° C. whereby the amount of discontinuous crystalline phase or average diameter of cubic leucite increases.

13. The method of claim 11 wherein said powder is heated at a temperature ranging from about 200° to below about 550° C. for a period of time sufficient to provide an amorphous material and thereafter reheating the amorphous material to a temperature of from about 550° to about 1200° C. at a heat-up rate ranging from about 0.5° to about 55° C./minute to provide a feldsphatic porcelain composition which comprises a continuous glassy matrix phase and a discontinuous crystalline phase comprising cubic leucite.

14. The method of claim 11 wherein said powder is heated at a temperature of at least about 550° C. and no higher than about 650° C. for a period of time sufficient to directly provide a feldspathic porcelain composition which comprises a continuous glassy matrix phase and a discontinuous crystalline phase comprising cubic leucite.

15. The method of claim 11 wherein the alkali aluminosilicate powder is formed by mixing a feldspar glass frit and metal salt in a weight ratio ranging from about 20:80 to about 80:20.

16. The method of claim 11 wherein the alkali silicate powder is formed by mixing a feldspar glass and metal salt in a weight ratio of about 50:50.

17. The method of claim 11 wherein the feldspathic glass frit comprises:

| Component | Weight Percent |
|---|---|
| $SiO_2$ | about 65 to about 72 |
| $Al_2O_3$ | about 9 to about 15 |
| $K_2O$ | about 5 to about 16 |
| $Na_2O$ | about 0.5 to about 10 |
| CaO | 0 to about 2 |
| MgO | 0 to about 2 |
| $CeO_2$ | 0 to about 0.5 |
| $Li_2O$ | 0 to about 2. |

18. The method of claim 11 wherein the metal salt is rubidium nitrate.

19. The method of claim 11 wherein the cubic leucite possesses an average diameter ranging from about 0.5 to about 10 microns.

20. The method of claim 11 wherein the cubic leucite possesses an average diameter ranging from about 1 to about 4 microns.

21. The method of claim 11 wherein the discontinuous crystalline phase comprises from about 5 to about 65 weight percent of the composition.

22. The method of claim 11 wherein an alkali metal salt is admixed with the metal salt to promote ion exchange.

23. The method of claim 22 wherein the alkali metal salt is admixed with the metal salt in amounts ranging from about 1 to about 10 weight percent of the metal salt.

24. A dental porcelain restoration comprising the feldspathic porcelain composition of claim 2.

25. A dental porcelain restoration comprising a framework and at least one coating fused thereon, said coating comprising the feldspathic porcelain composition of claim 2.

26. The dental porcelain restoration of claim 25 wherein the framework is a metal alloy.

27. A dental porcelain restoration comprising a ceramic core, said core comprising the feldspathic porcelain composition of claim 2.

28. An inlay, onlay or veneer comprising the feldspathic porcelain composition of claim 2.

29. The dental restoration of claim 24 in the form of a dental post.

30. A method of making a feldspathic porcelain composition which comprises the steps of providing an alkali aluminosilicate powder comprising a feldspathic glass frit comprising $SiO_2$, $Al_2O_3$, $K_2O$ and $Na_2O$ and at least one metal salt of rubidium, cesium, calcium, strontium and thallium;

heating the powder at a temperature in the range of from about 200° C. to about 900° C. to effect an exchange of alkali ions with metal ions derived from said metal salt;
thereafter heating the powder to a temperature in the range of from about 600° C. to about 1100° C. at a heat-up rate ranging from about 0.5° C./minute to about 55° C./minute to provide a feldspathic porcelain composition which comprises a continuous glassy matrix phase and a discontinuous crystalline phase comprising cubic leucite.

31. The method of claim 30 wherein the feldspathic glass frit and the metal salt are mixed in a weight ratio ranging from about 20:80 to about 80:20.

32. The method of claim 31 wherein the feldspar glass frit and metal salt are mixed in a weight ratio of about 50:50.

33. The method of claim 30 wherein the feldspathic glass frit comprises:

| Component | Weight Percent |
|---|---|
| $SiO_2$ | about 65 to about 72 |
| $Al_2O_3$ | about 9 to about 15 |
| $K_2O$ | about 5 to about 16 |
| $Na_2O$ | about 0.5 to about 10 |
| CaO | 0 to about 2 |
| MgO | 0 to about 2 |
| $CeO_2$ | 0 to about 0.5 |
| $Li_2O$ | 0 to about 2. |

34. The method of claim 30 wherein the metal salt is rubidium nitrate.

35. The method of claim 30 wherein an alkali metal salt is admixed with the metal salt to promote ion exchange.

36. The method of claim 35 wherein the alkali metal salt is admixed with the metal salt in amounts ranging from about 1 to about 10 weight percent of the metal salt.

37. The method of claim 30 further comprising treating the powder after ion exchange to substantially eliminate any unreacted metal salt.

38. A dental porcelain restoration comprising a feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}/°$ C. in the temperature range of 50 to 500° C. and wherein the leucite possesses an average diameter ranging from about 0.5 to about 10 microns.

39. The dental porcelain restoration of claim 38 wherein the cubic leucite comprises rubidium-stabilized cubic leucite.

40. A method of making a feldspathic porcelain composition which comprises the steps of providing an alkali aluminosilicate powder comprising a feldspathic glass frit comprising $SiO_2$, $Al_2O_3$, $K_2O$ and $Na_2O$ and at least one metal salt of rubidium, cesium, calcium, strontium and thallium;

heating the powder at a temperature of least about 550° C. and no higher than about 650° C. for a period of time sufficient to directly provide a feldspathic porcelain composition which comprises a continuous glassy matrix phase and a discontinuous crystalline phase comprising cubic leucite.

41. A dental porcelain restoration comprising a feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}$/° C. in the temperature range of 50 to 500° C. and wherein the leucite possesses an average diameter ranging from about 1 to about 4 microns.

42. A dental porcelain restoration comprising a feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}$/° C. in the temperature range of 50 to 500° C. and wherein the discontinuous crystalline phase comprises from about 5 to about 65 weight percent of the composition.

43. A dental porcelain restoration comprising a feldspathic porcelain composition comprising a continuous glassy matrix phase and a discontinuous, substantially uniformly dispersed crystalline phase which comprises cubic leucite, said composition possessing a fusion temperature of from about 800° to about 1200° C., having a coefficient of thermal expansion in the range of about 8 to about $16 \times 10^{-6}$/° C. in the temperature range of 50 to 500° C. and further comprising at least one additive selected from the group consisting of an opacifying agent, pigment and fluorescing agent.

* * * * *